United States Patent
Dininno et al.

[11] Patent Number: 5,182,385
[45] Date of Patent: * Jan. 26, 1993

[54] 2-BIPHENYL-CARBAPENEMS INTERMEDIATES

[75] Inventors: Frank P. Dininno, Old Bridge; Thomas N. Salzmann, North Plainfield, both of N.J.

[73] Assignee: Merck & Co., Inc., Rahway, N.J.

[*] Notice: The portion of the term of this patent subsequent to Jun. 18, 2008 has been disclaimed.

[21] Appl. No.: 594,767

[22] Filed: Oct. 9, 1990

[51] Int. Cl.$^5$ .................. C07D 487/04; C07F 7/10; A61K 31/40
[52] U.S. Cl. .................................. 540/302; 514/210
[58] Field of Search .................. 540/302; 514/210

[56] References Cited

U.S. PATENT DOCUMENTS

| | | | |
|---|---|---|---|
| 4,260,627 | 4/1981 | Christensen et al. | 514/240 |
| 4,465,632 | 8/1984 | Christensen et al. | 540/302 |
| 4,543,257 | 9/1985 | Cama et al. | 514/210 |
| 4,775,669 | 10/1988 | Cama et al. | 514/210 |
| 4,962,101 | 10/1990 | DiNinno et al. | 514/210 |
| 4,988,703 | 1/1991 | Norbeck et al. | 514/262 |
| 5,003,099 | 3/1991 | Mettler | 558/445 |
| 5,015,260 | 5/1991 | Tamura et al. | 568/706 |
| 5,023,250 | 6/1991 | Adams et al. | 514/179 |
| 5,025,006 | 6/1991 | Dininno et al. | 514/210 |
| 5,026,869 | 6/1991 | Flaugh | 548/436 |

FOREIGN PATENT DOCUMENTS 0277743  8/1988  European Pat. Off. .

OTHER PUBLICATIONS

L. D. Cama et al., Total Synthesis of Thienamycin Analogs-III, Tetrahedron 39, 2531 (1983).

R. N. Guthikonda, et al., Structure Activity Relationships in the 2-Arylcarbapenem Series, *J. Med. Chem.*, 30, 871 (1987).

*Primary Examiner*—Mukund J. Shah
*Assistant Examiner*—Jyothma Venkat
*Attorney, Agent, or Firm*—Curtis C. Panzer; Raymond M. Speer

[57] ABSTRACT

Carbapenems of the formula:

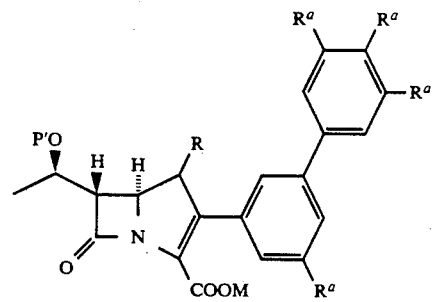

are useful intermediates to antibacterial agents.

3 Claims, No Drawings

2-BIPHENYL-CARBAPENEMS INTERMEDIATES

BACKGROUND OF THE INVENTION

The present invention relates to antibacterial agents of the carbapenem class, in which the 2-position sidechain is characterized by a biphenyl moiety, substituted by various substituents, as described in more detail further below.

The 2-biphenyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

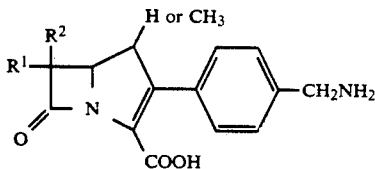

However, there is no description or suggestion of a biphenyl 2-substituent such as characterizes the compounds of the present invention, nor is there any suggestion of the suprisingly better anti-MRSA/MRCNS activity of the compounds of the present invention.

EP-A-0277 743 describes a particular class of compounds of the formula:

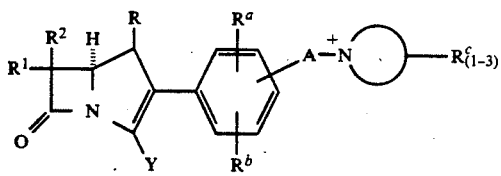

but this limited teaching in no way suggests the totally different compounds of the present invention, nor their surprisingly better anti-MRSA/MRCNS activity.

SUMMARY OF INVENTION

The present invention provides novel carbapenem compounds of the formula:

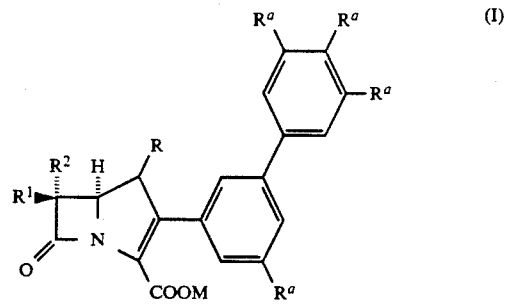

wherein:

R is H or $CH_3$;

$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;

$R^a$ are independently selected from the group consisting of hydrogen and the radicals set out below:

a) a trifluoromethyl group: —$CF_3$;

b) a halogen atom: —Br, —Cl, —F, or —I;

c) $C_1$-$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —C(O)$NH_2$, —OC(O)$NH_2$, CHO, —OC(O)N($CH_3$)$_2$, —$SO_2NH_2$, —$SO_2N(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;

e) a carbonyloxy radical: —O(C=O)$R^s$, where $R^s$ is $C_{1-4}$ alkyl or phenyl, each of which is optionally mono-substituted by $R^q$ as defined above;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —S(O)$_2$—, to form a ring (where the ring is optionally mono-substituted with Rq as defined above);

g) a sulfur radical: —S(O)$_n$—$R^s$ where n=0–2, and $R^s$ is defined above;

h) a sulfamoyl group: —$SO_2N(R^y)R^z$ where $R^y$ and $R^z$ are as defined above;

i) azido: $N_3$ j) a formamido group: —N($R^t$)(C=O)H, where $R^t$ is H or $C_{1-4}$ alkyl, and the alkyl thereof is optionally mono-substituted by $R^q$ as defined above;

k) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;

l) a ($C_1$-$C_4$ alkoxy) carbonylamino radical: —N($R^t$)(C=O)O$C_{1-4}$ alkyl, where $R^t$ is as defined above, and the alkyl group is also optionally mono-substituted by $R^q$ as defined above;

m) a ureido group: —N(R$^t$)(C=O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —(C=O)H or —CH(OCH$_3$)$_2$;

q) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as defined above;

r) carbonyl radical: —(C=O)R$^s$, where R$^s$ is as defined above;

s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring;

t) a (C$_1$-C$_4$ alkoxy)carbonyl radical: —(C=O)OC$_{1-4}$ alkyl, where the alkyl is optionally mono-substituted by R$^q$ as defined above;

u) a carbamoyl radical: —(C=O)N(R$^y$)R$^z$ where R$^y$ and R$^z$ are as defined above;

v) an N-hydroxycarbamoyl or N(C$_1$-C$_4$ alkoxy)-carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;

w) a thiocarbamoyl group: —(C=S)N(R$^y$)(R$^z$) where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono [P=O(OM$^b$)$_2$]; alkylphosphono {P=O(OM$^b$)—[O(C$_1$-C$_4$ alkyl)]}; alkylphosphinyl [P=O(OM$^b$)—(C$_1$-C$_4$alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_5$-C$_7$ cycloalkyl group in which one of the carbon atoms in the ring is replaced by a heteroatom selected from O, S, NH or N(C$_1$-C$_4$ alkyl) and in which one additional carbon atom may be replaced by NH or N(C$_1$-C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) C$_2$-C$_4$ alkenyl radical, optionally mono-substituted by one of the substituents a) to ac) above and phenyl which is optionally substituted by R$^q$ as defined above;

ae) C$_2$-C$_4$ alkynyl radical, optionally mono-substituted by one of the substituents a) to ac) above;

af) C$_1$-C$_4$ alkyl radical;

ag) C$_1$-C$_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and >NR$^t$ (where R$^t$ is as defined above) and one of the saturated carbon atoms of the oxazolidinone ring is optionally mono-substituted by one of the substituents a) to ag) above;

M is selected from:
i) hydrogen;
ii) a pharmaceutically acceptable esterifying group or removable carboxyl protecting group; or
iii) an alkali metal or other pharmaceutically acceptable cation.

Also provided are novel intermediates for carbapenem compounds of the formula:

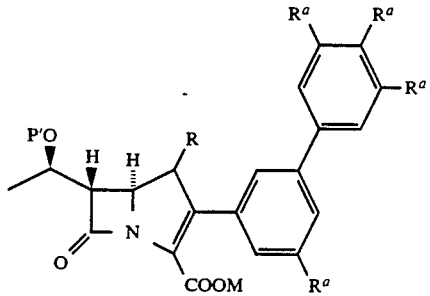

wherein:

R is H or CH$_3$;

R$^a$ is defined above, with the proviso that R$^q$ additionally includes OP' where P' is defined below, that M$^a$ and M$^b$ of R$^q$ both include M and that R$^a$ additionally may be protected hydroxy, OP';

M is a removable carboxyl protecting group; and

P' is a removable protecting group for hydroxy.

Preferred intermediates have the formula:

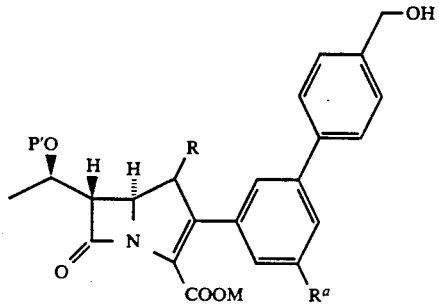

where

R is H or CH$_3$;

P' is a removable protecting group for hydroxy;

$R^a$ is selected from the group consisting of H, Cl, Br, I, SMe, CN, CHO, SOMe, SO$_2$Me, and OP'; and M is a removable protecting group for carboxyl.

DETAILED DESCRIPTION OF THE INVENTION

The manufacture of compounds of Formula I may be carried out in a three-stage synthesis scheme followed by a final step that allows for the removal of any protecting groups. The objective of the first synthetic stage is to produce a base biphenyl compound which may be converted to the two-position substituent of the carbapenem of Formula I. The objective of the second synthetic stage is to attach the base biphenyl to the carbapenem. Finally, the objective of the third synthetic stage is to substitute the biphenyl with the desired $R^a$. This third synthetic stage may either be performed after the first synthetic stage or during or after the second synthetic stage according to the nature of the various $R^a$.

Flow Sheets AA through AF demonstrate suggested first stage syntheses. Flow Sheets B and C demonstrate two alternative second stage syntheses. The third synthesis varies according to the selected $R^a$.

The suggested first synthesis herein, Flow Sheets AA through AF, show preparation of various 3-bromo biphenyls each designated as B1 for use in either Flow Sheet B or C. In one instance, an aryl stannane C3 is produced for use in Flow Sheet C. Following is a general description of the chemistry employed in each procedure.

AA: Synthesis of 3-bromo-5-substituted-biphenyls

A 3-bromo-5-substituted biphenyl intermediate is obtained by starting with a commercially available p-aminobiphenyl. The amino group serves to direct substitution to the two ortho positions (3 and 5), after which it can be removed reductively. However, in order to provide 5-substituted biphenyl compounds, the p-aminobiphenyl starting material AA1 as depicted in Flow Sheet AA is first protected by acetylation and then nitrated with nitrous acid before bromination is carried out.

Nitration is carried out with fuming nitric acid in the presence of acetic acid and acetic anhydride, after which deprotection is accomplished with sodium hydroxide using ethanol as a solvent and applying heat. These procedures are well known and are described in more detail, for example, in Dell'Erba et al., *Tetrahedron*, 27, 113 (1971).

Bromination is carried out in dioxane and water while the reaction mixture is maintained at near 0° C. with an ice-water bath. Aqueous 5N sodium hydroxide is added followed by bromine to produce compound AA2.

The original p-amino group is next removed by diazotization with sodium nitrite and concentrated sulfuric acid followed by reduction with powdered copper at ambient temperature to produce compound AA3.

The 5-nitro substituent is next converted to 5-amino group with stannous chloride dihydrate and this product then becomes the basis for obtaining a number of $R^a$ substituents on the meta-biphenyl moiety which characterize the compounds of the present invention. For example, the 5-fluoro compound can be obtained by thermal decomposition of the corresponding diazonium hexafluorophosphate salt, or the latter can be treated with potassium ethylxanthate to give the 5-ethylxanthylbiphenyl compound. This intermediate can then be the basis for obtaining the 5-methylthiobiphenyl compound of the present invention, or other unsubstituted and substituted alkyl mercaptans such as the 5-(2'-t-butyldimethylsilyloxyethylthio)biphenyl compound.

Returning to the diazotized 5-amino compound as a starting point for further synthesis, hydroxylation provides the 5-hydroxybiphenyl compound of the present invention, which can then be alkylated by treatment with sodium hydride followed by addition of an alkyl halide such as methyl iodide, to give the 5-alkoxy, e.g., 5-methoxybiphenyl compound of the present invention. The 5-hydroxy compound can also be protected by treatment with t-butyldimethysilyl chloride, creating an intermediate for synthesis of the desired hydroxybiphenyls of the present invention. The latter synthons, as the corresponding Grignard reagent or aryl stannane, allow for a meta-biphenyl moiety when attached to the carbapenem nucleus.

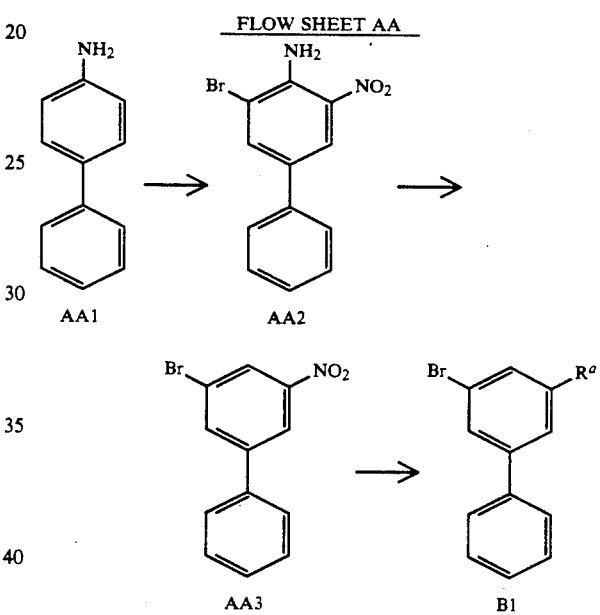

FLOW SHEET AA

AB: Synthesis of 3-bromo-4',5-disubstituted biphenyls

The 3-bromo-5-substituted biphenyls prepared in accordance with Flow Sheet AA above and also a simple 3-bromo biphenyl can be the starting point for introduction of a 4'-substituent in accordance with the following procedures. For example, the 4'-acetyl of the 3-bromo-5-fluoro compound can be made using the procedure of Berliner and Blommers, *JACS*, 73, 2479 (1951), after which, treatment with m-chloroperoxybenzoic acid in refluxing 1,2-dichloroethane gives the 3-bromo-4'-acetoxy-5-fluoro compound. Both of these compounds are compounds of the present invention.

The 4'-acetoxy compound can be converted to the 4'-hydroxy compound by treatment with sodium methoxide, and then protected using t-butyldimethylsilyl chloride in accordance with procedures described above, said protected compound being useful in further synthesis.

The 4'-acetyl compound can also be the starting point for conversion to other 3-bromo-5-fluoro-4'-substituted biphenyl compounds of the present invention. For example, oxidation with sodium hypobromite, provides the 4'-carboxyl group, which can then be converted by borane reduction to the corresponding alcohol, both compounds of the present invention. The 4'-hydroxymethyl compound can then be protected with t-butyldimethylsilyl chloride as described above, for use as an intermediate in synthesis of other 3-bromo-5-fluoro-4'-substituted biphenyls.

The 4'-acetyl compound can also be converted to an amino group by a Beckmann rearrangement process and hydrolysis, which in turn can be diazotized to provide diazonium salts capable of producing other 4'-substituents in the same fashion as described above.

FLOW SHEET AB

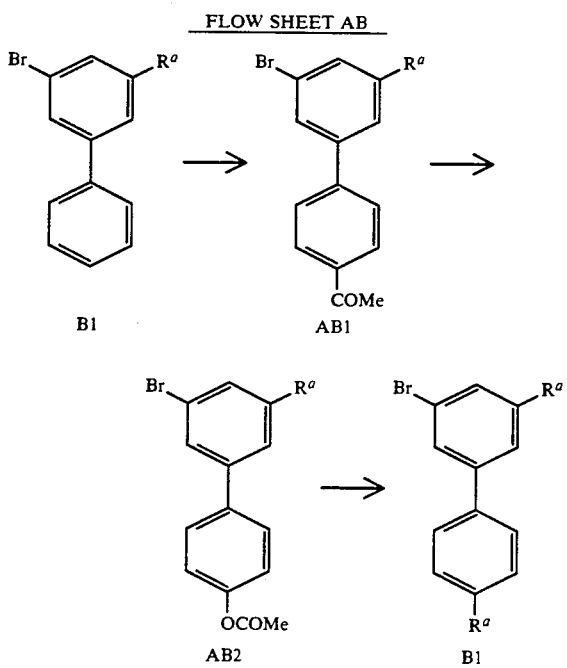

AC: Synthesis of 3-bromo-4',5',5-substitutedbiphenyls

Starting with the 3-bromo-4'-amino intermediate prepared as described in connection with Flow Sheet AB above, it is possible to prepare compounds of the present invention in which the 5'-position is substituted. Once a 4'-N-acetamido group is in place, it can be used to direct substitution of a nitro group which can be converted to various substituents, forming compounds of the present invention, in the same manner as was described above under Flow Sheet AA.

FLOW SHEET AC

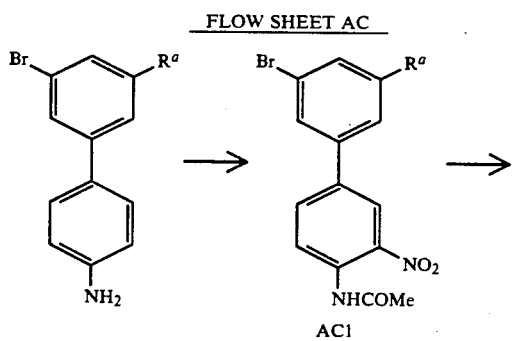

-continued
FLOW SHEET AC

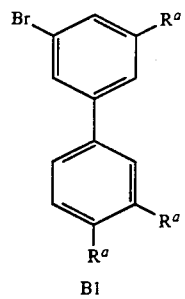

AD: Synthesis of 3-stannyl-3', 4', 5', 5-substituted biphenyl

Starting with 3-bromo-4'-acetamido5'-nitro intermediate, AC1, described above, it is possible to prepare biphenyl having 3', 4', 5' and 5 position substitution. Referring to Flow Sheet AD, intermediate AC1 is stannylated in a reaction with hexamethylditin in an aromatic hydrocarbon solvent, such as toluene or xylene, at elevated temperatures using tetrakistriphenylphosphinepalladium as a catalyst to produce intermediate AD1. Subsequently, the aryl stannane AD1 may be brominated in dioxane water at ambient temperatures or below to produce an aryl stannane AD2 with 3', 4', 5' and optional 5 position substitution. Each of these substituents, through subsequent art recognized procedures, may be replaced as desired to produce the aryl stannane C3, which may be employed in further synthesis of the carbapenems herein as according to Flow Sheet C below. Optionally, aryl stannane C3 may be converted to a Grignard Reagent analogous to B1.

FLOW SHEET AD

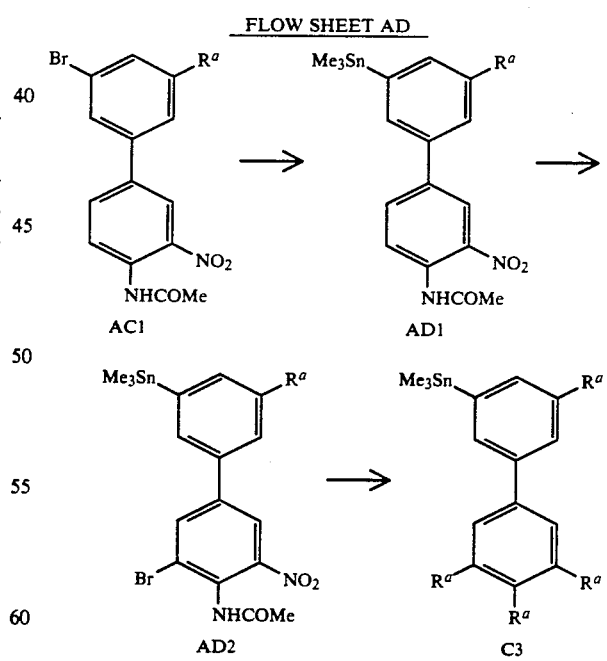

AE: Synthesis of 3-bromo-3', 4', 5'-substituted-biphenyls

Starting with readily available starting materials, 1,3-dibromobenzene and the appropriately substituted iodobenzene, it is possible to prepare biphenyls having 3', 4' and 5' position substitution. Referring to Flow Sheet AE 1,3-dibromobenzene AE1 is converted to boronic acid AE2 by first reacting with butyl lithium in anhydrous THF or ether at about −78° C. followed by addition of triisopropyl borate. The resultant intermediate is worked up with sodium hydroxide and acidified. Boronic acid AE2 is subsequently reacted with the appropriate iodobenzene AE3 in toluene and aqueous sodium carbonate with tetrakistriphenylphosphinepalladium as a catalyst to produce the 3-bromo biphenyl B1. This reaction to B1 is well known in art with reference made herein to N. Miyaura, T. Yanagi and A. Suzuki, *Syn. Comm.*, 11, 513 (1981).

FLOW SHEET AE

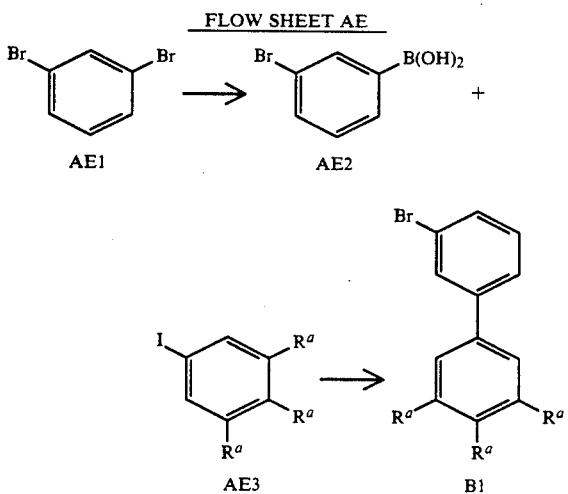

AF: Synthesis of 3-bromo-3',4',5'-substitutedbiphenyls

Alternatively, starting with readily available starting materials, difluorosilylbenzenes and, as above, iodobenzenes, it is possible to prepare biphenyls having 3', 4' and 5' position substitution. Referring to Flow Sheet AF, meta-bromoethyldifluorosilylbenzene AF1 is reacted in DMF with iodobenzene derivative AF2 and a desilylating agent, KF, using diallylpalladium chloride catalyst at elevated temperatures to produce 3-bromo biphenyl B1. This reaction is known in the art with reference made herein to Y. Hatanaka, S. Fukushima and T. Hiyama, *Chem. Lett.*, 1711 (1989).

FLOW SHEET AF

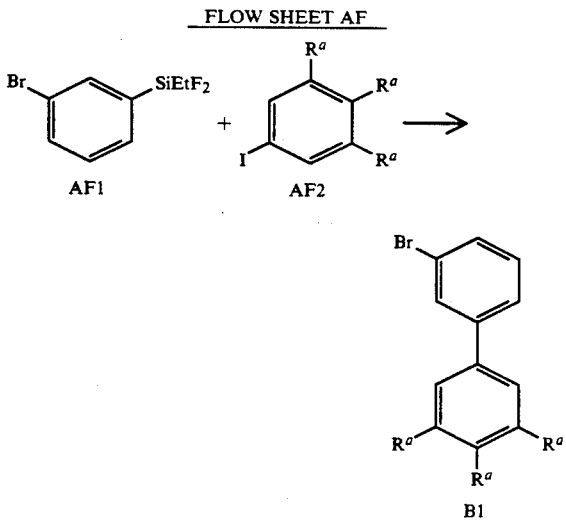

All of the above synthetic schemes relate to preparation of biphenyl compounds substituted at various positions to be used in the formation of Grignard reagents or aryl stannanes, which, in turn, as shown below, are used to couple the already substituted biphenyl compounds to the carbapenem nucleus just prior to its formation (ring closure), or with a suitably activated intact carbapenem synthon. However, it is immediately clear to those skilled in the art that certain $R^a$ listed above, if substituted on B1 or C3 may not be compatible with the second stage synthesis. Thus, it is also possible, as an alternative synthetic scheme for preparation of the compounds of the present invention, to generate the desired substituents at the appropriate positions on the biphenyl nucleus after the biphenyl nucleus itself has already been attached to the carbapenem nucleus. More precisely, however, this is a process of modifying compatible precursor substituents already in place on the biphenyl nucleus so as to convert them to additional desired substituents.

The identity of the precursor substituent where employed on B1 or C3 is not crucial and the precursor substituent may itself be a protected or unprotected $R^a$. Preferably the precursor substituent is compatible to the synthesis to B1 or C3. An incompatible precursor substituent would obviously require additional synthesis to make. Critically it is required that the precursor substituent is compatible with the chemistry depicted in Flow Sheets B and C and may be converted to more desireable substitution. Preferred precursor substituents are methyl, hydroxymethyl and protected hydroxymethyl for Flow Sheet B.

Thus, as to the $R^a$ substituent on compound B1 or C3, it may be an $R^a$ with or without protecting groups, preferably it is stable to the conditions of producing compound B1 or C3 and it must be stable to the conditions of subsequently adding B1 or C3 to the carbapenem. Alternatively, it may be a precursor substituent which is optionally stable to the conditions of making B1 or C3, which is stable to the conditions of adding B1 or C3 to the carbapenem and which is convertible to a desired $R^a$ or to another precursor substituent.

As stated above, the second stage synthesis is to attach the base biphenyl to the 2-position of the carbapenem. With stable $R^a$ or suitable precursor substituents therefore, biphenyl B1 may be added to azetidin-2-one B2 in a Grignard reaction as shown in Flow Sheet B. The Grignard reaction requires that B1 be converted to a Grignard reagent by reaction with magnesium and 1,2-dibromoethane in THF from 20° C. to 60° C. and subsequently contacting B1 as a Grignard reagent with B2 in THF at from −70° C. to about 20° C. to produce azetidin-2-one B3. Alternatively, B1 may be reacted with t-butyllithium, n-butyllithium, or the like in THF at from −78° to −50° C. followed by the addition of magnesium bromide to produce the same Grignard reagent. $R^i$ of B3 is in practice pyrid-2-yl but may clearly be a variety of substituents including aromatic and heteroaromatic substituents. Further $R^i$ might be for example phenyl, 2-pyrimidinyl or 2-thiazolyl.

Azetidin-2-one B3 is an intermediate that may be ring closed to a carbapenem. It is on this intermediate that $R^a$ or precursor substituent such as (t-butyldimethylsilyloxy)methyl may be modified where such modification is incompatible with the carbapenem nucleus. For example, a convenient reaction to remove a t-butyldimethylsilyl group of B3 is to expose it to 2% dilute solution of sulfuric acid in methanol at 0° C. for from a few minutes to several hours. If the t-butyldimethylsilyl group was removed from carbapenem B4 under the same conditions after cyclization of B3 to a carbapenem, a substantial portion of the carbapenem would be degraded and lost. Thus, modification of the precursor substituent in this instance and replacement with another precursor substituent or even $R^a$ is best performed before closing the carbapenem. Of course it is possible to remove the t-butyldimethylsilyl group in reduced yield after cyclization of B3 to a carbapenem by reaction with tetra-n-butylammonium fluoride and acetic acid in THF.

Compound B3 may be ring closed to carbapenem B4 by refluxing in xylene with a trace of p-hydroquinone for about 1 to 2 hours in an inert atmosphere. It is on this intermediate that final elaboration of $R^a$ from a precursor substituent, e.g. hydroxymethyl, may be accomplished. Removal of the carboxyl and hydroxyl protecting groups then provides the final compound Formula I. Such final elaboration and deprotection is described in further detail below.

FLOW SHEET B

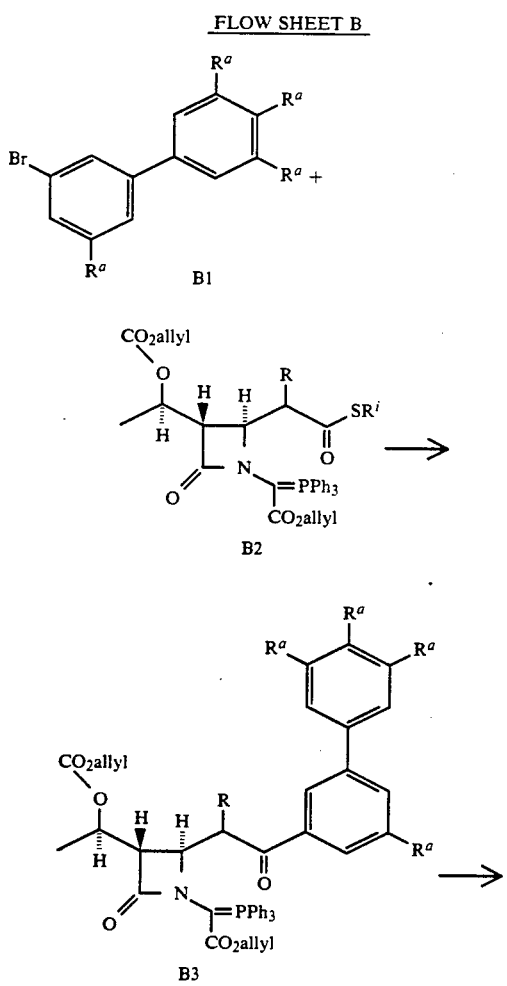

-continued
FLOW SHEET B

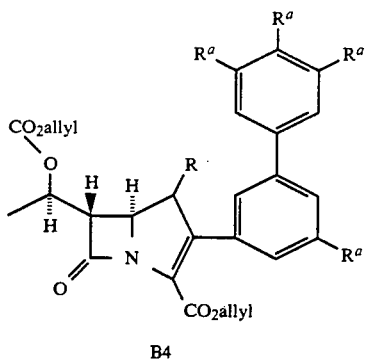

B4

Flow Sheet C shows an alternative second stage synthesis, i.e. attachment of the base biphenyl such as B1 to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990, hereby incorporated by reference. In order to apply this synthesis, it is first necessary to modify bromobiphenyl B1 to the trimethylstannylbiphenyl C3. This is accomplished by reacting B1 with t-butyllithium in THF at from −78° to −50° C. followed by the addition of trimethyltin chloride. Alternatively, C3 may be prepared by simply heating B1 with hexamethylditin in the presence of tetrakistriphenylphosphine palladium in toluene solution. At this intermediate, it may be desireable to remove certain protecting groups if employed on a precursor substituent $R^a$. For instance, a protecting group such as t-butyldimethylsilyl on a hydroxymethyl substituent may be removed by exposure to tetra-n-butylammonium fluoride in THF yielding a particular C3. If the t-butyldimethylsilyl group was removed from carbapenem C4 under the same conditions, a substantial portion of the carbapenem would be degraded and lost. Thus modification of the precursor substituent in this instance and replacement with another precursor substituent or even $R^a$ is best performed before attachment to the carbapenem. Referring again to Flow Sheet C, the 2-oxocarbapenam C1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran or methylene chloride. An organic nitrogen base, such as triethylamine and the like, is then added to the reaction solution followed immediately by a silylating agent, such as trimethylsilyl trifluoromethanesulfonate to provide intermediate C2. An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate and the like, a suitably substituted phenylphosphine, such as tris(4-methoxyphenyl)phosphine, tris(2,4,6-trimethoxyphenyl)phosphine and the like, and the stannane C3. A metal halide, such as lithium chloride, zinc chloride and the like, is added and the reaction solution is allowed to warm and is stirred at a suitable temperature, such as 0° to 50° C., for from a few minutes to 48 hours. The carbapenem C4 is obtained by conventional isolation/purification methodology known in the art.

in U.S. Pat. Nos. 4,260,627 and 4,543,257; L. D. Cama et al. *Tetrahedron*, 39, 2531 (1983); R. N. Guthikonda et al. *J. Med. Chem.*, 30, 871 (1987) hereby incorporated by reference.

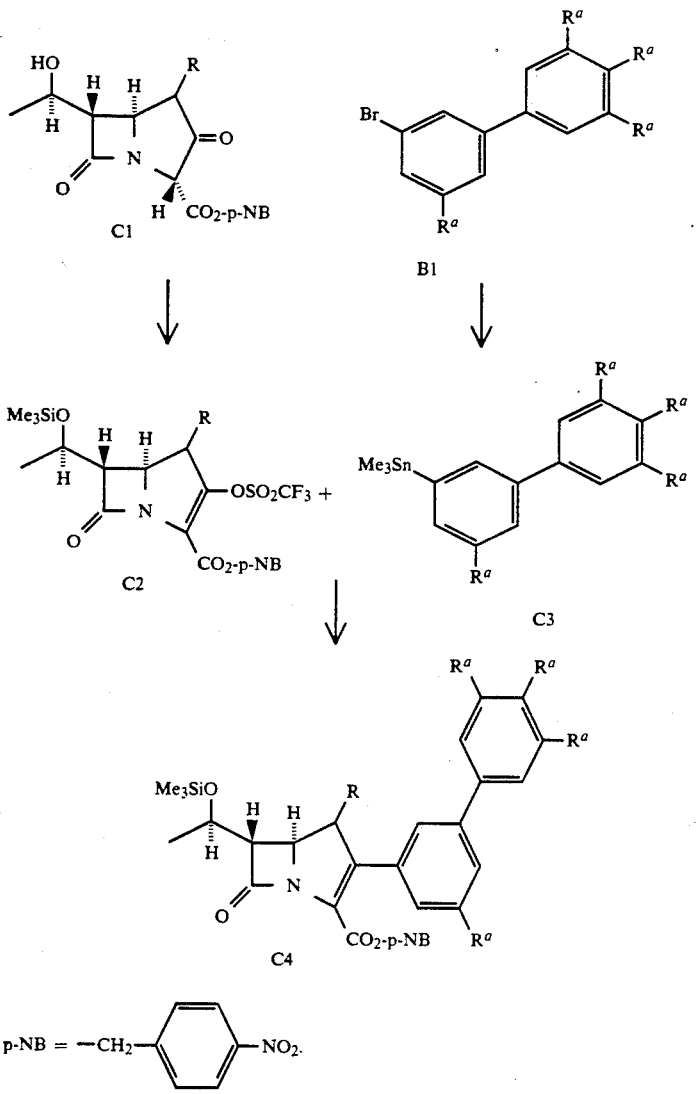

FLOW SHEET C

Generally speaking, the milder conditions of the synthesis shown in Flow Sheet C allow for a wider range of functional groups $R^a$ to be present than the synthesis illustrated in Flow Sheet B. However, in certain cases, it is advantageous fo the $R^a$ substituent(s) of the stannane C3 to be introduced in a protected or precursory form. Final elaboration of $R^a$ from a precursor substituent, e.g. hydroxymethyl, may be accomplished on carbapenem intermediate C4. Removal of hydroxyl and ester protecting groups then provides the final compound of Formula I. Such final elaboration and deprotection is described in further detail below.

Azetidin-2-one B2, a pyridyl-thioester, is a well known compound in the production of carbapenems. Diverse synthetic schemes useful to make B2 may be imagined by the skilled artisan. Particularly useful to the instant invention is a synthetic scheme set out further in Flow Sheet D below in which the symbol R is as defined above. The steps for preparing intermediate B2 are analogous to the procedures described, for example,

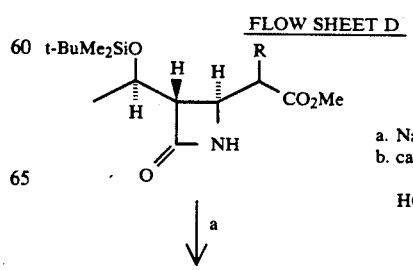

FLOW SHEET D a. NaOH/MeOH
b. carbonyl diimidazole/

FLOW SHEET D (continued)

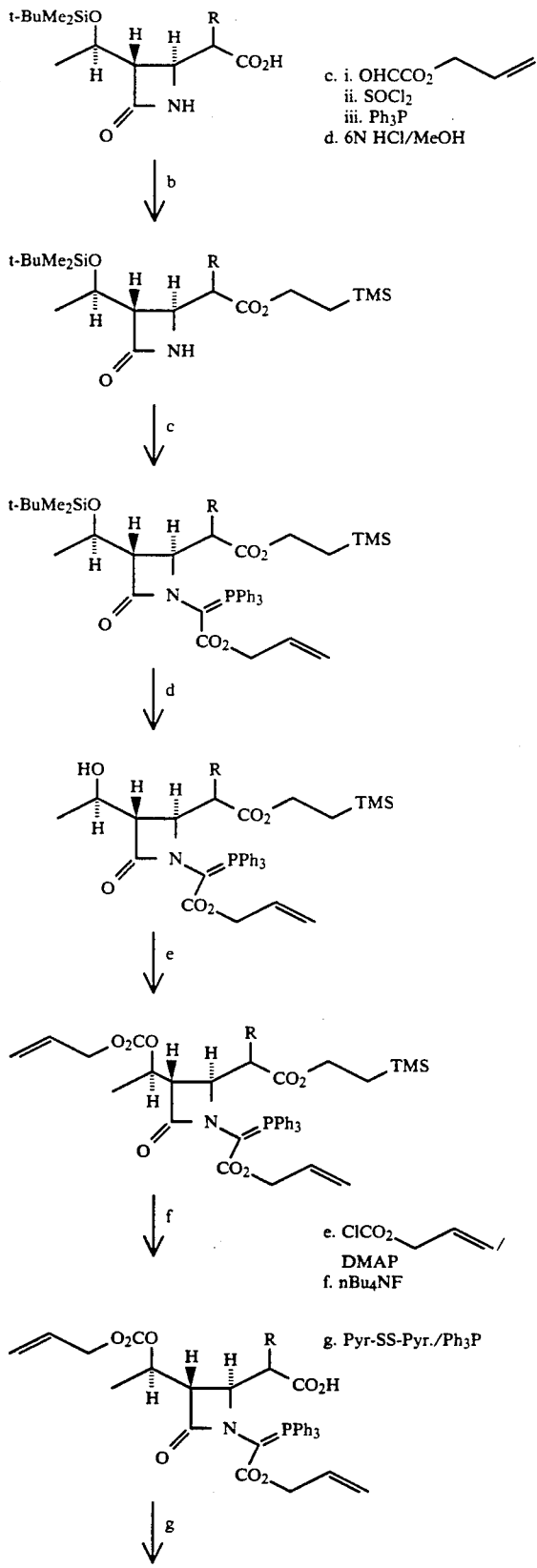

c. i. OHCCO₂⬥
   ii. SOCl₂
   iii. Ph₃P
d. 6N HCl/MeOH e. ClCO₂⬥
   DMAP
f. nBu₄NF g. Pyr-SS-Pyr./Ph₃P

FLOW SHEET D -continued

B2

The steps for preparing the 2-oxocarbapenam intermediate C1 are well known in the art and are explained in ample detail by D. G. Melillo et al., *Tetrahedron Letters*, 21, 2783 (1980), T. Salzmann et al., *J. AM. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc. and hereby incorporated by reference.

The general synthesis description depicted above in the Flow Sheets shows a protected 1-hyroxyethyl substitution on the 6-position of the carbapenem. After final deprotection, a 1-hydroxyethyl substituent is obtained, which is preferred in most cases. However, it has been been found that with certain 2-side-chain selections the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanruku Ocean).

In preferred compounds of Formula I, either $R^1$ or $R^2$ is hydrogen and more preferably, $R^1$ is hydrogen. In the most preferred case, $R^1$ is hydrogen and $R^2$ is (R)—CH₃CH(OH)— or (R)—CH₃CH(F)—. While R=H is usually preferred, there are instances in which R=CH₃ may provide improved chemical stability, water solubility, or pharmacokinetic behavior. The substituent R=CH₃ may be of either configuration, i.e., the α or β-stereoisomer. Additionally, in preferred compounds, $R^a$ in the 5- position of the biphenyl is other than hydrogen.

Suitable $R^a$ are described above in the text associated with Formula I. Among preferred $R^a$ are $C_{1-4}$ alkyl mono-substituted with hydroxy, such as, hydroxymethyl; formyl; carboxy, such as, —COOK; carbamoyl, such as, —CONH₂; hydroxyiminomethylene, such as, —CH=NOH or cyano.

In regard to this preferred substitution, one or more hydroxymethyl groups may be obtained on the biphenyl ring as desired utilizing well known synthetic methods. For example where biphenyl is produced according to Flow Sheet AE, then a methyl group, as a precursor substituent, is substituted on starting materials AE1 and/or AE2 in the appropriate positions by well known means and the starting materials reacted to a corresponding B1. Subsequently, the methyl substituent of B1 may be oxidized e.g. to a carboxylic acid group with chromium trioxide or to bromomethyl group with N-bromosuccinimide. This oxidation of the methyl precursor substituent, may be advantageously performed prior to substituting the biphenyl on the azetidin-2-one as the oxidizing conditions may be incompatible with either the azetidin-2-one or the subsequent carbapenem. The carboxylic acid group may be converted to a hydroxymethyl group utilizing a borane tetrahydrofuran complex and the bromomethyl by conversion to acetoxymethyl group with potassium acetate followed by hydrolysis. As another example where the biphenyl is produced according to Flow Sheets AA through AD, an amino substituent might be converted to a halogen which is then transformed to a carboxylic acid moiety and subsequently to hydroxymethyl group as described above and all by well known reactions.

The preferred formyl substitution on the biphenyl may be obtained from the hydroxymethyl substitution of B4 by a Swern oxidation. For example, isomeric B4 is oxidized in methylene chloride at from −70° C. to room temperature employing triethylamine and as the active agent, oxalyl chloride-dimethyl sulfoxide. Obviously, the position of the resultant formyl substitution will depend upon the position of the hydroxymethyl substitution in isomeric B4.

The preferred —CH=NOH substitution on the biphenyl may be conveniently obtained from the formyl substitution just described. This is accomplished simply by exposing the formyl substituted compound to hydroxylamine in an appropriate solvent at room temperature.

The preferred cyano substitution on the biphenyl may be obtained from the —CH=NOH substitution just described. The —CH=NOH substituted compound is dehydrated with triflic anhydride and triethylamine in a solvent at −70° C.

The preferred —COOK substitution on the biphenyl may be obtained from the hydroxymethyl substituted B3 or isomeric B3 described above. For example, an isomeric B3 is oxidized with Jones reagent to convert the hydroxymethyl substituent to the carboxylic acid group. The oxidation with Jones reagent may be incompatible with the carbapenem and thus is optimally performed before ring closure. Prior to ring closure, the carboxylic acid group is protected as its allyl ester to permit cyclization of the carbapenem. Protection is carried out by alkylating with allyl bromide and triethylamine. Deprotection following cyclization is carried out in a palladium catalyzed reaction, in a solution containing potassium 2-ethylhexanoate, as described in McCombie and Jeffrey, *J. Org. Chem.*, 47, 2505 (1983). Deprotection in such a solution yields the desired potassium salt.

The preferred carbamoyl, —CONH$_2$, may be obtained from B3 by oxidizing the hydroxymethyl group with Jones reagent to the corresponding carboxylic acid group as described above. This carboxylic acid substituent is converted to carboxamide group (—CONH$_2$) by sequentially contacting with 1-ethyl-3-(3-dimethyl-aminopropyl)carbodiimide hydrochloride, 1-hydroxybenzotriazole, and ammonia in an organic solvent at room temperature. Substituted amides may of course be obtained by replacing ammonia with the corresponding substituted amine. In contrast to the carboxyl substitution, this carbamoyl group requires no protection for the conditions of carbapenem cyclization.

Compounds substituted with the preferred R$^a$ of Type II just described may also be obtained by employing the synthesis shown in Flow Sheet C. In this case, the synthetic transformations just described may be carried out on intermediate C3 prior to attachment of the biphenyl side-chain to carbapenem or on C4 after such attachment.

In the preparation methods described above, the carboxyl group at the 3-position and the hydroxyl group at the 8-position of the carbapenem remain blocked by protecting groups until the penultimate product is prepared. Suitable hydroxyl protecting groups, P', are triorganosilyl groups such as trialkylsilyl, aryl(alkyl)silyl, and diarylalkylsilyl and carbonate groups such as alkyloxycarbonyl and substituted alkyloxycarbonyl, benzyloxycarbonyl and substituted benzyloxycarbonyl and allyloxycarbonyl and substituted allyloxycarbonyl. The preferred protecting groups are methoxy-t-butylphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups, M, in addition to or including those shown in the schemes are described herein below.

Deblocking may be carried out in a conventional manner. For compounds prepared according to Flow Sheet B, deprotection may be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet C, deprotection is conducted sequentially. Thus, compound C4 is exposed initially to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as NaHCO$_3$ or KHCO$_3$ and 10% Pd/C followed by hydrogenation provides for the removal of the p-nitrobenzyl protecting group and the formation of the final compound of Formula I.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the R$^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N+1 O or 1 S). While additional nitrogen atoms may be present together with the first nitrogen and oxygen or sulfur, giving, e.g., a thiadiazole (2N's+1S), the preferred heteroaryls are those where only nitrogen heteroatoms are present when there is more than one. Typical of these are pyrazole, imidazole, pyrimidine and pyrazine (2N's) and triazine (3N's).

The heteroaryl group of R$^x$ is always optionally mono-substituted by R$^q$, defined above, and substitution can be on one of the carbon atoms or one of the heteroatoms, although in the latter case certain substitutent choices may not be appropriate.

Listed in Tables I and II are specific compounds of the instant invention:

TABLE I

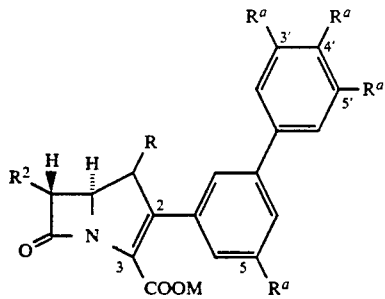

| # | R | R² | M | Rᵃ | Ra position |
|---|---|---|---|---|---|
| 1 | —H | (R)—CH(OH)CH₃ | K⁺ | —OCH₃ | 5 |
| 2 | —H | (R)—CH(OH)CH₃ | K⁺ | —OCH₂CO₂Na | 5 |
| 3 | —H | (R)—CH(OH)CH₃ | K⁺ | —OCH₂CH₂OH | 5 |
| 4 | —H | (R)—CH(OH)CH₃ | K⁺ | —CF₃ | 5 |
| 5 | —H | (R)—CH(OH)CH₃ | Na⁺ | —F | 5 |
| 6 | —H | (R)—CH(OH)CH₃ | K⁺ | —Cl | 5 |
| 7 | —H | (R)—CH(OH)CH₃ | K⁺ | —Br | 5 |
| 8 | —H | —CH₂OH | K⁺ | —I | 5 |
| 9 | β-CH₃ | (R)—CH(OH)CH₃ | K⁺ | —OH | 5 |
| 10 | —H | (R)—CH(OH)CH₃ | K⁺ | —OCOCH₃ | 5 |
| 11 | —H | (R)—CH(OH)CH₃ | K⁺ | —OCONH₂ | 5 |
| 12 | —H | (R)—CH(OH)CH₃ | K⁺ | —SCH₃ | 5 |
| 13 | —H | (R)—CH(F)CH₃ | K⁺ | —SOCH₃ | 5 |
| 14 | β-CH₃ | (R)—CH(OH)CH₃ | K⁺ | —SO₂CH₃ | 5 |
| 15 | —H | (R)—CH(OH)CH₃ | Na⁺ | —SCH₂CH₂OH | 5 |
| 16 | —H | (R)—CH(OH)CH₃ | K⁺ | —SOCH₂CH₂OH | 5 |
| 17 | —H | (R)—CH(OH)CH₃ | K⁺ | —SO₂CH₂CH₂OH | 5 |
| 18 | —H | (R)—CH(OH)CH₃ | Na⁺ | —SO₂NH₂ | 5 |
| 19 | —H | (R)—CH(OH)CH₃ | K⁺ | —SO₂N(CH₃)₂ | 5 |
| 20 | —H | —CF₂CH₃ | K⁺ | —NHCHO | 5 |
| 21 | β-CH₃ | (R)—CH(OH)CH₃ | K⁺ | —NHCOCH₃ | 5 |
| 22 | —H | (R)—CH(OH)CH₃ | K⁺ | —NHCO₂CH₃ | 5 |
| 23 | —H | (R)—CH(OH)CH₃ | K⁺ | —NHSO₂CH₃ | 5 |
| 24 | —H | (R)—CH(OH)CH₃ | K⁺ | —CN | 5 |
| 25 | —H | (R)—CH(OH)CH₃ | K⁺ | —CHO | 5 |
| 26 | —H | —CH₂OH | K⁺ | —COCH₃ | 5 |
| 27 | —H | (R)—CH(OH)CH₃ | K⁺ | —COCH₂OH | 5 |
| 28 | —H | (R)—CH(OH)CH₃ | K⁺ | —CH=NOH | 5 |
| 29 | —H | (R)—CH(OH)CH₃ | K⁺ | —CH=NOCH₃ | 5 |
| 30 | α-CH₃ | (R)—CH(OH)CH₃ | K⁺ | —CH=NOCH₂CO₂H | 5 |
| 31 | α-CH₃ | —CH₂CH₃ | K⁺ | —CH=NOCMe₂CO₂H | 5 |
| 32 | —H | (R)—CH(OH)CH₃ | K⁺ | —CH=NOCMe₂CO₂Me | 5 |
| 33 | —H | (R)—CH(OH)CH₃ | K⁺ | —CO₂CH₂CH₂OH | 5 |
| 34 | —H | (R)—CH(OH)CH₃ | K⁺ | —CONH₂ | 5 |
| 35 | —H | (R)—CH(OH)CH₃ | K⁺ | —CONHCH₃ | 5 |
| 36 | —H | (R)—CH(OH)CH₃ | K⁺ | —CON(CH₃)₂ | 5 |
| 37 | —H | (R)—CH(OH)CH₃ | K⁺ | —CONHCH₂CN | 5 |
| 38 | β-CH₃ | —CF₂CH₃ | K⁺ | —CONHCH₂CONH₂ | 5 |
| 39 | —H | (R)—CH(OH)CH₃ | K⁺ | —CONHCH₂CO₂H | 5 |
| 40 | —H | (R)—CH(OH)CH₃ | Na⁺ | —CONHOH | 5 |
| 41 | —H | (R)—CH(OH)CH₃ | K⁺ | —CONHOCH₃ | 5 |
| 42 | —H | (R)—CH(OH)CH₃ | K⁺ | -tetrazolyl | 5 |
| 43 | —H | —CH₂OH | K⁺ | —CO₂Na | 5 |
| 44 | —H | (R)—CH(OH)CF₃ | K⁺ | —SCF₃ | 5 |
| 45 | —H | (R)—CH(OH)CH₃ | K⁺ | —PO₃NaH | 5 |
| 46 | —H | (R)—CH(OH)CH₃ | K⁺ | —CONHSO₂Ph | 5 |
| 47 | β-CH₃ | (R)—CH(OH)CH₃ | K⁺ | —CONHSO₂NH₂ | 5 |
| 48 | —H | (R)—CH(OH)CH₃ | K⁺ | —SO₃Na | 5 |
| 49 | —H | (R)—CH(OH)CH₃ | K⁺ | —SO₂NHCN | 5 |
| 50 | β-CH₃ | (R)—CH(F)CH₃ | K⁺ | —SO₂NHCONH₂ | 5 |
| 51 | —H | (R)—CH(OH)CH₃ | K⁺ | —CH=CHCN | 5 |
| 52 | —H | (R)—CH(OH)CH₃ | K⁺ | —CH=CHCONH₂ | 5 |
| 53 | —H | (R)—CH(OH)CH₃ | K⁺ | —CH=CHCO₂Na | 5 |
| 54 | —H | (R)—CH(OH)CH₃ | Na⁺ | —C≡C—CONH₂ | 5 |
| 55 | β-CH₃ | (R)—CH(OH)CH₃ | K⁺ | —C≡C—CN | 5 |
| 56 | —H | (R)—CH(OH)CH₃ | K⁺ | —CH₂OH | 4' |
| 57 | —H | —CH₂CH₃ | K⁺ | —CH₂N₃ | 5 |
| 58 | —H | (R)—CH(OH)CH₃ | K⁺ | —CH₂CO₂Na | 5 |
| 59 | —H | (R)—CH(OH)CH₃ | Na⁺ | —SOCH₃ | 5 |
| 60 | —H | (R)—CH(OH)CH₃ | Na⁺ | —SO₂CH₃ | 5 |
| 61 | —H | (R)—CH(OH)CH₃ | Na⁺ | —NHCHO | 5 |
| 62 | —H | (R)—CH(OH)CH₃ | Na⁺ | —NHCOMe | 5 |
| 63 | —H | (R)—CH(OH)CH₃ | Na⁺ | —COCH₃ | 5 |
| 64 | —H | (R)—CH(OH)CH₃ | Na⁺ | —COCF₃ | 5 |
| 65 | —H | (R)—CH(OH)CH₃ | Na⁺ | —COCH₂CONH₂ | 5 |

TABLE I-continued

| # | R | R² | M | Rᵃ | Rᵃ position |
|---|---|---|---|---|---|
| 66 | —H | (R)—CH(OH)CH₃ | Na⁺ | —CH₂CONH₂ | 5 |
| 67 | —H | (R)—CH(OH)CH₃ | Na⁺ | —CONHCH₂CONH₂ | 5 |
| 68 | —H | (R)—CH(OH)CH₃ | Na⁺ | —SCF₃ | 5 |
| 69 | —H | (R)—CH(OH)CH₃ | Na⁺ | —CONHSO₂NH₂ | 5 |
| 70 | —H | (R)—CH(OH)CH₃ | Na⁺ | —OCH₂CH₂OH | 4' |
| 71 | —H | (R)—CH(OH)CH₃ | Na⁺ | —OCH₂CH₂OH | 5' |
| 72 | —H | (R)—CH(OH)CH₃ | Na⁺ | —OCOCH₃ | 4' |
| 73 | —H | (R)—CH(OH)CH₃ | Na⁺ | —OCOCH₃ | 3' |
| 74 | —H | (R)—CH(OH)CH₃ | Na⁺ | —OCONH₂ | 4' |
| 75 | —H | (R)—CH(OH)CH₃ | Na⁺ | —SCH₂CH₂OH | 5' |
| 76 | —H | (R)—CH(OH)CH₃ | Na⁺ | —SCH₂CH₂OH | 4' |
| 77 | —H | (R)—CH(OH)CH₃ | Na⁺ | —SCH₂CH₂OH | 3' |
| 78 | —H | (R)—CH(OH)CH₃ | Na⁺ | —CHO | 4' |
| 79 | —H | (R)—CH(OH)CH₃ | Na⁺ | —CHO | 3' |
| 80 | —H | (R)—CH(OH)CH₃ | Na⁺ | —CHO | 5,4' |
| 81 | —H | (R)—CH(OH)CH₃ | Na⁺ | —COCH₂OH | 4' |
| 82 | —H | (R)—CH(OH)CH₃ | Na⁺ | —SO₂N(CH₂CH₂OH)₂ | 5 |
| 83 | —H | (R)—CH(OH)CH₃ | Na⁺ | —CON⟨thiomorpholinyl⟩ | 5 |
| 84 | —H | (R)—CH(OH)CH₃ | Na⁺ | —CON⟨pyrrolidinyl⟩ | 5 |
| 85 | —H | (R)—CH(OH)CH₃ | Na⁺ | —CON⟨morpholinyl⟩ | 5 |
| 86 | —H | (R)—CH(OH)CH₃ | Na⁺ | —CO₂Me | 5 |
| 87 | —H | (R)—CH(OH)CH₃ | Na⁺ | —F | 3' |
| 88 | —H | (R)—CH(OH)CH₃ | Na⁺ | —CH=ⁱCHCN | 4' |
| 89 | —H | (R)—CH(OH)CH₃ | Na⁺ | —CH=ⁱCHCONH₂ | 4' |
| 90 | —H | (R)—CH(OH)CH₃ | Na⁺ | —CN | 4' |
| 91 | —H | (R)—CH(OH)CH₃ | Na⁺ | —OH | 3' |
| 92 | —H | (R)—CH(OH)CH₃ | Na⁺ | —OH | 4' |
| 93 | —H | (R)—CH(OH)CH₃ | Na⁺ | —CH₂SMe | 4' |
| 94 | —H | (R)—CH(OH)CH₃ | Na⁺ | —OCONH₂ | 3' |
| 95 | —H | (R)—CH(OH)CH₃ | Na⁺ | —SOMe | 4' |
| 96 | —H | (R)—CH(OH)CH₃ | Na⁺ | —SO₂CH₃ | 4' |
| 97 | —H | (R)—CH(OH)CH₃ | Na⁺ | —SMe | 4' |
| 98 | —H | (R)—CH(OH)CH₃ | Na⁺ | —CH=ᶜCHCN | 4' |
| 99 | —H | (R)—CH(OH)CH₃ | Na⁺ | —OH | 3',4' |
| 100 | —H | (R)—CH(OH)CH₃ | Na⁺ | —OH | 3',4',5' |
| 101 | —H | (R)—CH(OH)CH₃ | Na⁺ | —OH | 5,3',4' |
| 102 | —H | (R)—CH(OH)CH₃ | Na⁺ | —F | 5,4' |
| 103 | —H | (R)—CH(OH)CH₃ | Na⁺ | —F | 5,3' |
| 104 | —H | (R)—CH(OH)CH₃ | Na⁺ | —SMe | 5,3' |
| 105 | —H | (R)—CH(OH)CH₃ | Na⁺ | —SMe | 5,4' |

TABLE II

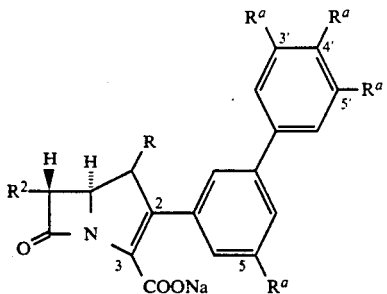

| R¹ | R² | R$^a$ 5 | 5' | 4' | 3' |
|---|---|---|---|---|---|
| —H | (R)—CH(OH)CH$_3$ | —CHO | —H | —OH | —H |
| —H | (R)—CH(OH)CH$_3$ | —CHO | —H | —F | —H |
| —H | (R)—CH(OH)CH$_3$ | —CHO | —CHO | —F | —H |
| —H | (R)—CH(OH)CH$_3$ | —SCH$_3$ | —H | —OH | —H |
| —H | (R)—CH(OH)CH$_3$ | —SCH$_3$ | —H | —SOCH$_3$ | —H |
| —H | (R)—CH(OH)CH$_3$ | —SCH$_3$ | —CHO | —H | —H |
| —H | (R)—CH(OH)CH$_3$ | —SCH$_3$ | —H | —CH$_2$OH | —H |
| —H | (R)—CH(OH)CH$_3$ | —CONH$_2$ | —H | —CHO | —H |
| —H | (R)—CH(OH)CH$_3$ | —CONH$_2$ | —F | —CHO | —H |
| —H | (R)—CH(F)CH$_3$ | —CONH$_2$ | —H | —CH$_2$OH | —H |
| β-CH3 | (R)—CH(OH)CH3 | —CONH$_2$ | —H | —SOCH$_3$ | —H |
| —H | —CH$_2$OH | —SCH$_3$ | —H | —CHO | —H |
| —H | (R)—CH(OH)CH$_3$ | —CN | —H | —SOCH$_3$ | —H |
| —H | (R)—CH(OH)CH$_3$ | —CN | —H | —CONH$_2$ | —H |
| —H | (R)—CH(OH)CH$_3$ | —CN | —H | —OH | —OH |
| —H | (R)—CH(OH)CH$_3$ | —CN | —H | —CHO | —H |
| —H | (R)—CH(OH)CH$_3$ | —SO$_2$CH$_3$ | —H | —CHO | —H |
| —H | (R)—CH(OH)CH$_3$ | —SO$_2$CH$_3$ | —H | —OCNH$_2$ | —H |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium' magnesium, zinc, ammonium, or alkylammonium cations such as tetramethylammonium, tetrabutylammonium, choline, triethylhydroammonium, meglumine, triethanolhydroammonium, etc.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protectimg groups include benzhydryl, p-nitrobenzyl, 2-naphthylmethyl, allyl, benzyl, trichloroethyl, silyl such as trimethylsilyl or t-butyldiphenylsilyl, phenacyl, p-methoxybenzyl, acetonyl, o-nitrobenzyl and 4-pyridylmethyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they mey be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1) define the procedure for determining DHP susceptibility of the present carbapenems and 2) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxyamide)-2-heptenoic acid or a useful salt thereof.

Unless otherwise indicated, all of the temperatures in the working examples which follow are in degrees Celsius (°C).

EXAMPLE 1

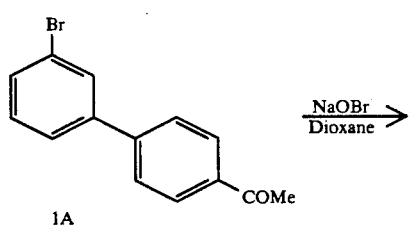

1A

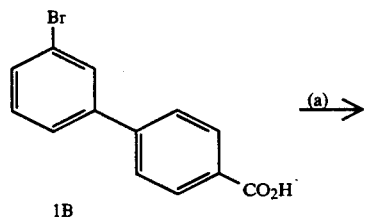

1B

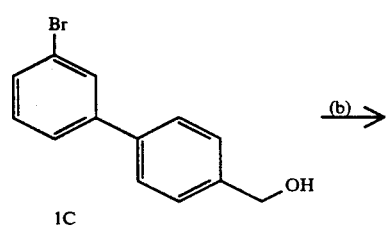

1C

-continued

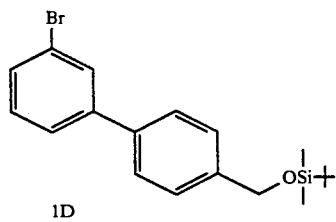
1D

Step (a)

To a stirred partial solution of 2.13 g (7.68 mmole) of carboxylic acid derivative 1B, prepared according to D. J. Byron, et al, *J. Chem. Soc.* (C), 840 (1966), in 40 cc of freshly distilled, dry THF at ambient temperature was added slowly and cautiously a solution of 1M borane-tetrahydrofuran complex in THF (15.4 mL, 15.4 mmole). The resulting mixture was stirred overnight at ambient temperature under an inert atmosphere of nitrogen and then carefully quenched with methanol. The solution was evaporated under reduced pressure and the residue dried in vacuo to give ca. 2 g (100%) of crude alcohol 1C which may be used without further purification.

Purification of 1C can be formed on silica gel utilizing $CH_2Cl_2$-$Et_2O$ (20:1) as the eluant; NMR ($CDCl_3$) δ: 4.74 (s, $-CH_2O-$), 7.42-7.72 (m, 8Ar—H).

Step (b)

To a stirred solution of 2.3 g (8.9 mmole) of carbinol 1C from step (a) in 25 mL of sieve dried DMF at ambient temperature was added 1.35 g (13.4 mmole) of triethylamine and 2.02 g (13.4 mmole) of t-butyldimethylsilyl chloride. The resulting mixture was stirred at room temperature under an inert atmosphere of nitrogen for 1.5 hours. After this time, the mixture was partitioned between $Et_2O$/ice-$H_2O$/2N HCl and the organic phase was separated. It was washed twice with ice-$H_2O$ and then with a saturated solution of sodium chloride; dried with anhydrous sodium sulfate, filtered, and evaporated.

Purification by column chromatography on silica gel eluting with petroleum-ether (30°-60° C.) —$CH_2Cl_2$ (10:1) provided 3.16 g (94%) of product 3; NMR ($CDCl_3$) δ: 0.12 (s, $Si(CH_3)_2$), 0.96 (s, $SiC(CH_3)_3$), 4.78 (s, $OCH_2$), 7.32-7.74 (m, Ar—H).

EXAMPLE 2

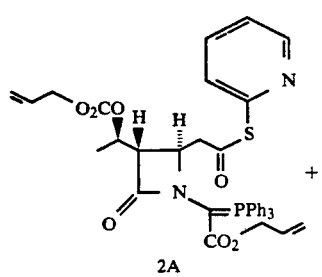
2A

-continued

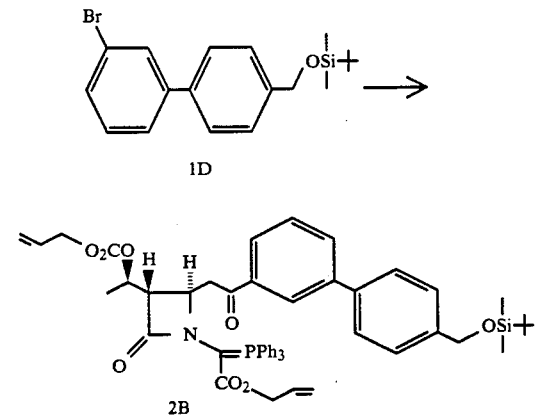
1D

2B

A stirred solution of 1D (562 mg, 1.49 mmole) in 5 mL freshly distilled, dry THF was treated with 54.5 mg (2.23 mmole) of magnesium turnings and 5 µl dibromoethane at ambient temperature in an inert atmosphere of nitrogen for 5.5 hours. This solution of the Grignard reagent was then added to a solution of pyridylthio ester derivative 2A (527.8 mg, 0.75 mmole) in 5 mL dry THF at 0° C. under a nitrogen atmosphere. The resulting mixture was stirred at 0° C. for 15 minutes and then partitioned between EtOAc/ice/1M $NH_4Cl(aq.)$ and the organic phase separated. It was washed with ice-$H_2O$/5N NaOH and then saturated sodium chloride solution, dried with anhydrous sodium sulfate, filtered, and evaporated under reduced pressure.

Purification by plate layer chromatography (PLC) eluting with $Et_2O$ gave 501.2 mg (75%) of 2B; IR($CH_2Cl_2$) 1745, 1685, 1610 cm$^{-1}$.

EXAMPLE 3

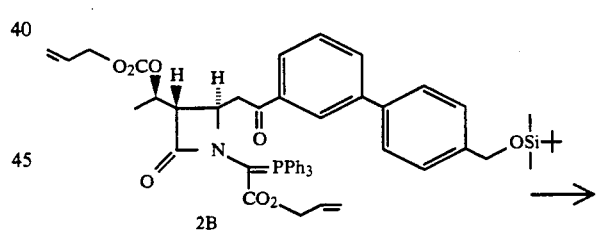
2B

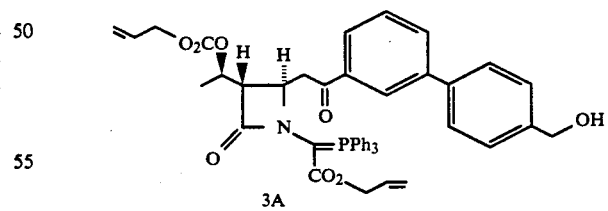
3A

A mixture of 501.2 mg (0.56 mmole) of phosphorane 2B, prepared in Example 2, and 160 µL concentrated sulfuric acid in 8 mL of methanol was stirred magnetically at 0° C. in an inert atmosphere of nitrogen for 1.0 hour. After this time, the mixture was partitioned between EtOAc/ice-$H_2O$/satd. $NaHCO_3$ (aq.) solution and the organic phase was separated, washed with saturated sodium chloride solution, dried over sodium sulfate, filtered, evaporated, and dried in vacuo to give 443 mg (>100%) of crude product 3A, which could be used without further purification; IR(CH2Cl2) 1745, 1675, 1610 cm⁻¹.

EXAMPLE 4

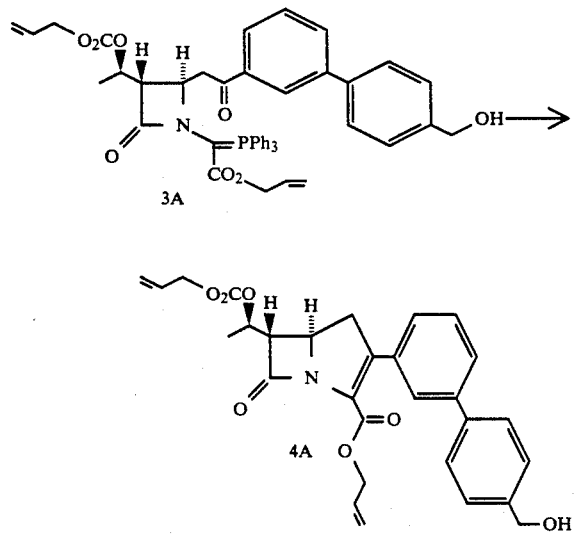

A stirred solution of crude phosphorane 3A (437.4 mg, 0.56 mmole), prepared in Example 3, in 30 mL of dry xylenes containing a crystal of hydroquinone was heated at 140° C. under an atmosphere of nitrogen for 84 minutes. After this time the mixture was let cool and then it was evaporated under reduced pressure.

Purification of the residue by PLC [one development CH2Cl2/EtOAc (5:1)] gave 190.5 mg (68%) of 4A as an oil; IR(CH2Cl2) 1770, 1750, 1725 cm⁻¹; NMR(CDCl3) δ: 1.51 (d, CH3), 3.25 (dd, 1-H-1), 3.47 (dd, 1-H-1), 3.45 (dd, 1-H-6), 4.31 (dt, 1-H-5), 4.76 (bs, 2H,—CH2OH), 7.3-7.58 (m, 8-ArH); UV: $\lambda_{max}^{dioxane}$ 307 nm.

EXAMPLE 5

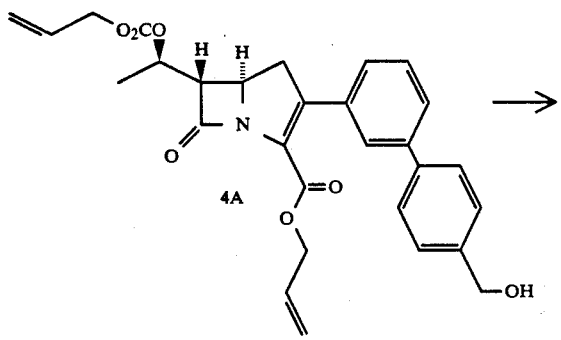

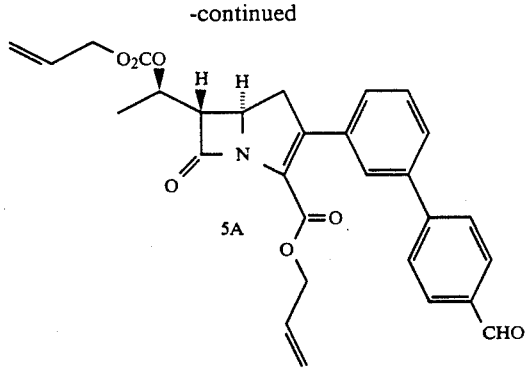

To a stirred solution of 19 μL (0.22 mmole) of oxalyl chloride in 1.5 ml anhydrous CH2Cl2 at −78° C. under a N2 atmosphere was added 19.7 μL (0.27 mmole) of anhydrous DMSO. The resulting solution was stirred at −78° C. for 4 minutes and then a solution of 100 mg (0.20 mmole) of alcohol 4A in 1.0 mL anhydrous CH2Cl2 was added. The resulting yellow solution was stirred at −78° C. for 15 minutes and then 76 μL (0.55 mmole) of triethylamine was added. The resulting solution was stirred at −78° C. for 25 minutes and then partitioned between EtOAc and ice/2. ON aqueous HCl solution. The organic phase was separated, washed with brine, dried with anhydrous Na2SO4, filtered and concentrated under vacuum to provide 94.4 mg of aldehyde 8 as a yellow film; IR(CH2Cl2): 1780, 1745, 1720, 1700 cm⁻¹; 300 MHz ¹H-NMR(CDCl3) δ: 1.50 (d, J=8.2 Hz, CH3), 3.31 (m, 2-H-1), 3.45 (dd, J=2.8, 8.4 Hz, 1-H-6) 4.31 (td, 1-H-5), 4.67 (m, 1-H-8 and CH2CH=CH2), 5.29 (m, CH2CH=CH2), 5.90 (m, CH2CH=CH2), 7.37-7.98 (m, phenyl-H), 10.08 (s, —CHO).

EXAMPLE 6

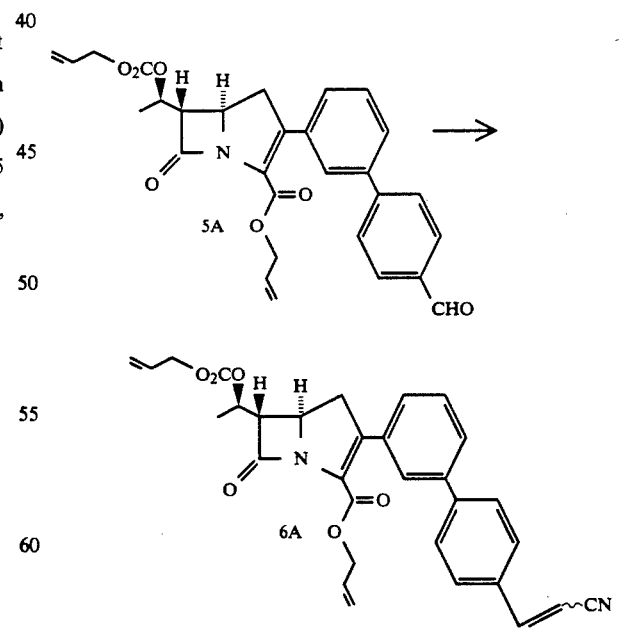

To a stirred solution of 94.4 mg (0.19 mmole) of aldehyde 5A in 4 mL anhydrous acetonitrile at 0° C. under a N2 atmosphere was added 102 mg (0.34 mmole) of cyanomethylene triphenylphosphorane. The resulting solution was stirred at room temperature for 3 hours and then concentrated under vacuum to provide a yellow film which was purified by PLC (2×1000μ 20×20 cm silica gel GF; 1:1, hexanes: EtOAc) to provide two products: trans 6A, 44.6 mg of a clear film; IR(CH2Cl2): 2210, 1780, 1745, 1720 cm$^{-1}$; 300 MHz NMR (CDCl3) δ: 1.50 (d, J=6.2 Hz, CH3), 3.30 (m, 2H-1), 3.44 (dd, J=2.9, 8.4 Hz, CHCHC=O), 4.32 (td, CHCHCH2), 4.65 (m, 1H-8 and CH2CH=CH2), 5.30 (m, CH2CH=CH2), 5.87 (m, CH2CH=CH2), 5.92 (d, J=16.5 Hz, CH=CHCN), 7.27–7.63 (m, phenyl-H and CH=CHCN). UV: $\lambda_{max}^{dioxane}$ 309 nm; and cis 6A: 22.3 mg of a clear film; 300 MHz NMR (CDCl3): δ: 5.48 (d, J=12.1 Hz, CH=CHCN), 7.68 (d, J=12.1 Hz, CH=CHCN).

EXAMPLE 7

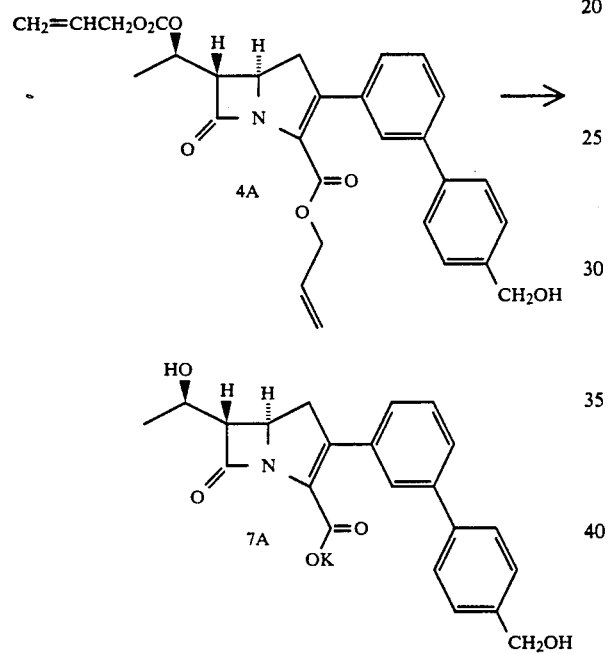

To a stirred solution of 100.6 mg (0.2 mmole) of 4A in 6 mL of CH2Cl2-EtOAc (1:1) at ambient temperature was added 31.5 mg (0.12 mmole) of triphenylphosphine, 46.2 mg (0.04 mmole) of tetrakistriphenylphosphine palladium, 31.7 mg (0.22 mmole) 2-ethylhexanoic acid, and 440 μL of 0.5M potassium 2-ethylhexanoate in EtOAc (0.22 mmole). The resulting mixture was stirred at ambient temperature under a nitrogen atmosphere for 2.5 hours. The separated product was triturated with 8 mL of Et2O-EtOAc (1:1) and collected by centrifugation and decantation of the supernatant. The solid was washed similarly with 10 mL Et2O and dried to give 109.4 mg of crude product.

Purified by reverse phase-plate layer chromotography on two-1000μ plates [one development H2O-MeCN (5:1)] to give after extraction with MeCN-H2O (4:1) and lyophilization 37.6 mg (45%) of 7A; IR (Nujol) 1750 and 1595 cm$^{-1}$; NMR (D2O) δ: 1.32 (d, Me), 3.12 (dd, 1-H-1), 3.48 (app dd, 1-H-1), 3.54 (app dd, 1-H-6), 4.34 (m, H-5 and H-8), 4.72 (s, 2H), 7.6 (m, 8-Ar-H); UV: 80 max H2O 297 nm, 257 nm.

EXAMPLE 8

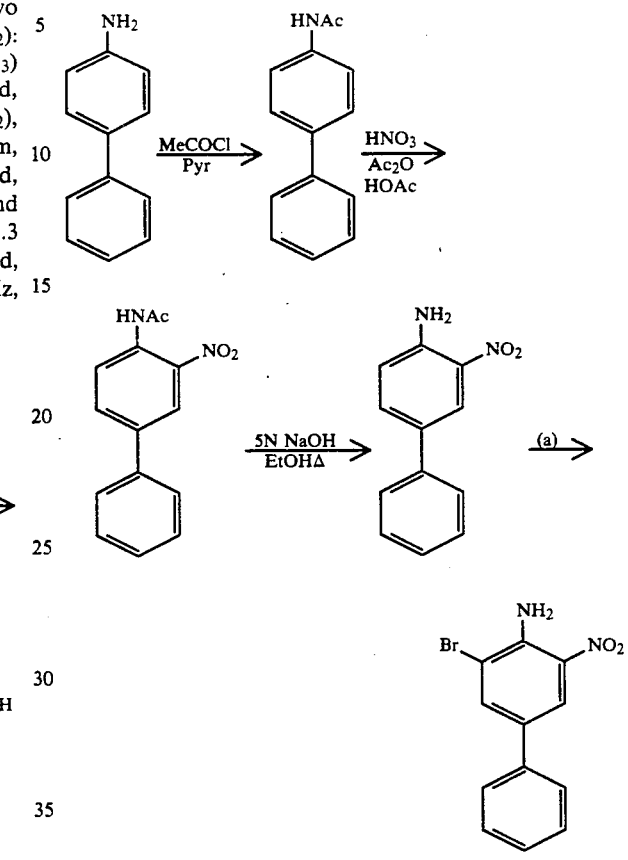

Step (a)

To a stirred solution of 3-nitro-4-amino-biphenyl (13.85 g, 64.7 mmole) [prepared according to a the procedures described in C. Dell'Erba, G. Garbarino, and G. Guanti, Tetrahedron, 27, 113 (1971).] in 230 mL dioxane and 77 mL H2O cooled in an ice-H2O bath was added sequentially 12.9 mL 5N NaOH (aq.) (64.7 mmole) and then dropwise 12.41 g (77.7 mmole) bromine. When the addition was complete, the ice-H2O bath was removed, and the mixture stirred further for 2 hours. After this time, the mixture was concentrated under high vacuum, H2O added, and the insoluble material collected by suction filtration and washed with H2O. The solid was dried in vacuo to give 19.6 g of crude product.

Recrystallization from MeOH-CH2Cl2-pet.ether gave only 8.78 g (46.5%) of 3-bromo-4-amino-5-nitrobiphenyl; NMR (CDCl3) δ: 6.65 (bs, 2 NH), 7.44 (m, 5 Ar-H), 7.98 (d, 1-Ar-H), and 8.38 (d, 1-Ar-H).

Chromatography on silica gel of the mother liquors using CH2Cl2-pet.ether (1:1) as eluant gave an additional 7.6 g of product for a combined yield of 86.7%.

EXAMPLE 9

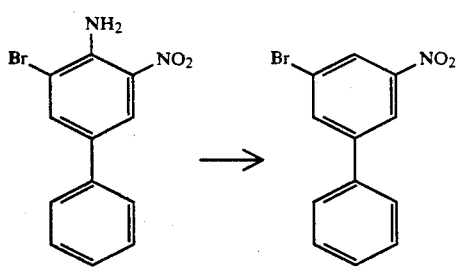

To a stirred solution of 759 mg (11 mmole) of sodium nitrite in 15 mL concentrated sulfuric acid chilled in an ice-H$_2$O bath was added a solution of 2.92 g (10 mmole) of biphenylamine derivative from Example 9 in 30 mL hot glacial HOAc. The resulting mixture was stirred at ice-H$_2$O bath temperature for 20 minutes.

The ice-H$_2$O bath was removed, 1.27 g (20 mmole) copper powder added, and the mixture stirred further for 2 hours. The insolubles were removed by suction filtration through a preformed pad of celite and washed with Et$_2$O. The filtrate was partitioned between Et$_2$O-/ice-H$_2$O/5N NaOH and the organic phase was separated, washed with saturated NaCl solution, dried Na$_2$SO$_4$, filtered, and evaporated.

The residue was purified by chromatography on 50 grams of EM-60 silica gel eluted with petroleum ether-CH$_2$Cl$_2$ (2:1) to give 2.2 g (80%) of 3-bromo-5-nitrobiphenyl; NMR (CDCl$_3$) δ: 7.54 (m, 5 Ar-H), 8.05 (d, 1 Ar-H), 8.34 (d, 1 Ar-H), and 8.38 (d, 1 Ar-H).

EXAMPLE 10

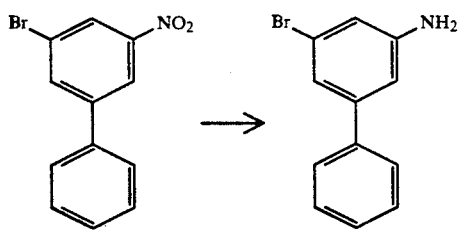

A stirred mixture of 7.62 g (27.5 mmole) of 3-bromo-5-nitrobiphenyl and 18.62 g (82.5 mmole) of stannous chloride dihydrate in 150 mL of absolute ethanol was refluxed under a nitrogen atmosphere for 1.5 hours. After this time, the mixture was concentrated and partitioned between Et$_2$O/ice/5N NaOH. The organic phase was separated, washed with saturated NaCl solution, dried over Na$_2$SO$_4$, filtered, and evaporated.

The product was purified by chromatography on silica gel with CH$_2$Cl$_2$-petroleum ether (1:1) to give 5.9 g (87%) of 3-bromo-5 aminobiphenyl; NMR (CDCl$_3$) δ: 3.8 (bs 2NH), 6.82 (m, 1Ar-H), 7.15 (t, 1Ar-H), 7.48 (m, 6Ar-H).

EXAMPLE 11

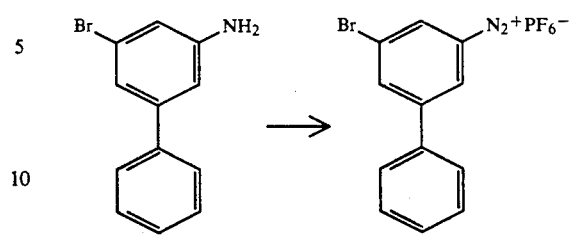

To a stirred solution of 1.08 g (15.6 mmole) of NaNO$_2$ in 10 mL conc. H$_2$SO$_4$ cooled in an ice-H$_2$O bath was added dropwise a solution of 3.67 g (14.9 mmole) of 3-bromo-4-aminobiphenyl in 40 mL HOAc. When the addition was complete, the mixture was stirred further for 10 minutes at 0° C., and then 4.0 g (21.7 mmole) of KPF$_6$ in 43 mL H$_2$O was added. The resulting mixture was stirred cold for 10 minutes and the separated product collected by suction filtration; washed well with cold H$_2$O and then with 80 mL Et$_2$O-MeOH (4:1); dried in vacuo overnight to give 5.87 g (97%) of diazonium hexafluorophosphate derivative; mp 157° C. (dec); IR (Nujol) 2295 cm$^{-1}$; NMR (d$_6$-DMSO) δ: 7.66 (m, 3Ar-H), 7.88 (m, 2Ar-H), 8.88 (m, 1Ar-H), 9.0 (m, 1Ar-H), and 9.16 (m, 1Ar-H).

EXAMPLE 12

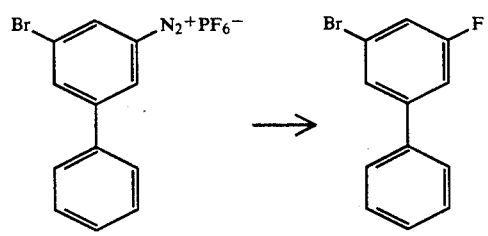

A stirred suspension of 4.04 g (10 mmole) of diazonium salt in 40 mL decane under a nitrogen atmosphere was immersed in a 170° C. oil bath for 10 minutes. The mixture was allowed to cool and then filtered through celite and washed with Et$_2$O. The filtrate was partitioned between Et$_2$O/ice-H$_2$O/saturated NaHCO$_3$(aq.) solution and the organic phase separated, washed with saturated NaCl solution, dried over Na$_2$SO$_4$, filtered, and evaporated.

The residue was purified by chromatography on silcia gel with petroleum ether solvent to give 2.51 g (100%) of 3-bromo-5-fluorobiphenyl; NMR (CDCl$_3$) δ: 7.2 (m, 2Ar-H) and 7.48 (m, 6Ar-H); MS: m/e 252, 250 (M+).

EXAMPLE 13

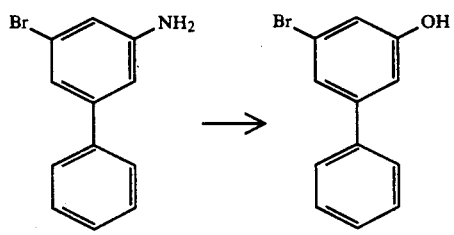

As previously described in Example 12, 1.24 g (5 mmole) of 3-bromo-5-aminobiphenyl was diazotized with 380 mg (5.5 mmole) of NaNO$_2$ in 4 mL conc. H$_2$SO$_4$ and 10 mL HOAc. The the stirred mixture was added 10 mL H$_2$O and it was heated at 70° C. under a nitrogen atmosphere for 1.25 hours.

The cooled mixture was partitioned between Et$_2$O-H$_2$O, and the organic phase separated, washed with H$_2$O (2×), then ice/saturated, NaHCO$_3$(aq.) solution and saturated NaCl solution; dried over Na$_2$SO$_4$, filtered and evaporated.

The residue was purified by column chromatography on silica gel with CH$_2$Cl$_2$-petroleum ether (1:1) and CH$_2$Cl$_2$-petroleum ether (3:1) to provide 995 mg (80%) of 3-bromo-5-hydroxy-biphenyl; NMR (CDCl$_3$) δ: 5.32 (bs, OH), 7.02 (m, Ar-H) and 7.4 (m, Ar-H).

EXAMPLE 14

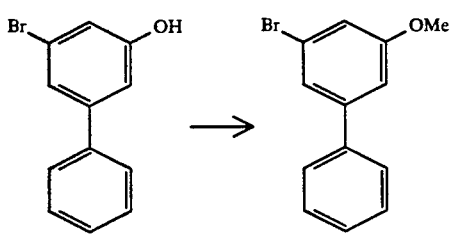

To a stirred solution of 995 mg (4 mmole) of 3-bromo-4-hydroxybiphenyl in 10 mL sieve dried DMF at ambient temperature was added 173.3 mg (4.4 mmole) of 61.1% mineral oil dipersion of NaH. The resulting mixture was stirred at room temperature under a nitrogen atmosphere for 10 minutes and 1.71 g (12 mmole) of neat MeI was added. The mixture was stirred further at ambient temperature for 0.5 hour.

The mixture was poured onto ice-H$_2$O and extracted with Et$_2$O. The extract was washed with ice-H$_2$O (2×), and then saturated NaCl solution; dried over Na$_2$SO$_4$, filtered, and evaporated.

The residue was purified by silica gel chromatography with petroleum ether solvent to give 842 mg (80%) of 3-bromo-5-methoxybiphenyl; NMR (CDCl$_3$) δ: 3.87 (s, OCH$_3$), 7.07 (m, 2Ar-H), 7.48 (m, 6Ar-H).

EXAMPLE 15

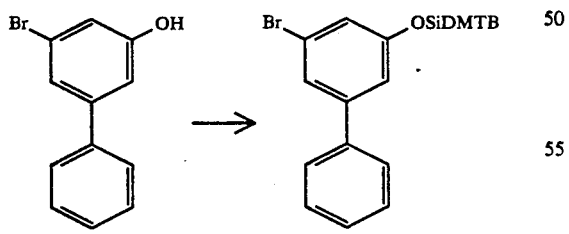

To a stirred solution of 372 mg (1.5 mmole) of 3-bromo-5-hydroxybiphenyl and 339.1 mg (2.25 mmole) of t-butyldimethylsilyl chloride in 4 mL sieve dried DMF at ambient temperature under a nitrogen atmosphere was added 227.7 mg (2.25 mmole) of triethylamine. The resulting mixture was stirred further for 1.75 hours.

The mixture was partitioned between Et$_2$O/ice-H$_2$O/2N HCl (aq.) and the organic phase separated, washed with ice-H$_2$O (3×), and saturated NaCl solution, dried over NaSO$_4$, filtered, and evaporated.

The residue was purified by PLC [1 development petroleum ether] to give 500 mg (92%) of 3-bromo-5-t-butyldimethylsilyloxybiphenyl; NMR (CDCl$_3$) δ: 0.14 (s, Si(CH$_3$)$_2$), 1.0 (s, SiC(CH$_3$)$_3$), 6.98 (m, Ar-H), and 7.44 (m, Ar-H).

EXAMPLE 16

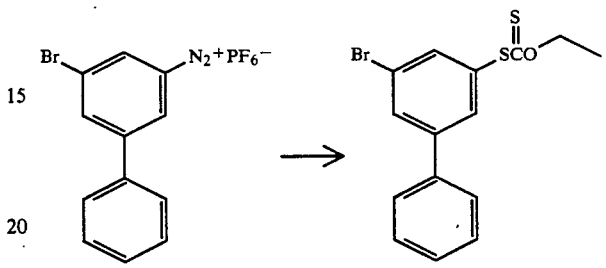

To a stirred solution of 11.1 g (69,4 mmole) of potassium ethylxanthate in 120 mL acetone at 0° C. under a nitrogen atmosphere was added all at once 20 g (49.4 mmoles) of biphenyldiazonium salt from Example 11. The mixture was stirred 1.3 hours at 0° C. and 0.75 hours at ambient temperature. The mixture was partitioned between Et$_2$O/ice-H$_2$O and the organic phase was separated, washed with brine, and dried over Na$_2$SO$_4$/MgSO$_4$, filtered, and evaporated to a brown oil. The residue was purified by silica gel chromatography to give 3.5 g of pure 3-bromo-5-ethylxanthylbiphenyl; NMR (CDCl$_3$) δ: 1.36 (t, CH$_3$), 4.62 (q, OCH$_2$), 7.3–7.7(m, Ar-H).

EXAMPLE 17

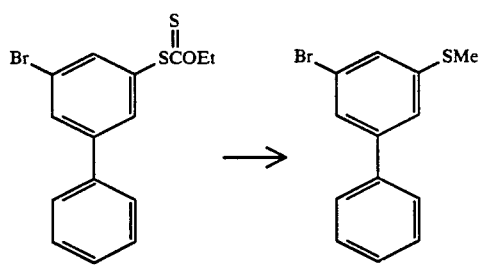

To a stirred solution of 10.79 g (30.7 mmole) of xanthate derivative from Example 16 in 140 mL of anhydrous THF at 0° C. under a nitrogen atmosphere was added 6.1 mL (92 mmole) of ethylene diamine and the mixture stirred further for 10 minutes. After this time, 5.4 mL (86 mmole) of methyl iodide was added, the ice-H$_2$O bath removed, and the mixture stirred 1 hour longer.

The mixture was partitioned between Et$_2$O/ice-H$_2$O and the organic phase separated, washed with brine, dried over Na$_2$SO$_4$/MgSO$_4$, filtered, and evaporated.

The residue was purified by distillation to give 5.82 (68%) of 3-bromo-5-methylthiobiphenyl; NMR (CDCl$_3$) δ: 2.55 (s, SCH$_3$), 7.36–7.56 (m, Ar-H); MS: m/e 280, 278 (M$^+$).

EXAMPLE 18

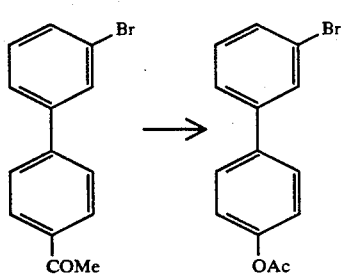

A stirred mixture of 1.19 g (5.84 mmole) of 85% m-chloroperoxybenzoic acid and 1.24 g (4.49 mmole) of 3-bromo-4'-acetylbiphenyl [prepared according to E. Berliner and E. A. Blommers, *JACS*, 73, 2479 (1951)] in 15 mL 1,2-dichloroethane was refluxed under a nitrogen atmosphere for 17 hours.

The cooled mixture was partitioned between Et$_2$O-/ice-H$_2$O/5% Na$_2$S$_2$O$_3$ (aq.) solution and the organic phase separated, washed with ice-H$_2$O/saturated NaHCO$_3$ (aq.) solution and then saturated NaCl solution, dried over Na$_2$SO$_4$, filtered, and evaporated.

The residue was purified by PLC [one development CH$_2$Cl$_2$-petroleum ether] to give 1.09 g (83%) of 3-bromo-4-acetoxy-biphenyl; NMR (CDCl$_3$) δ: 2.33 (s, OAc), 7.14–7.7 (m, Ar-H).

EXAMPLE 19

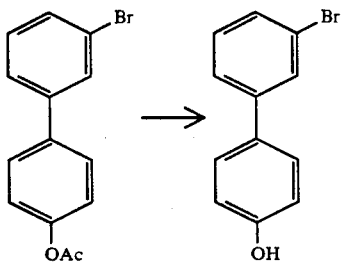

To a stirred solution of 1.07 g (3.67 mmole) of 3-bromo-4-acetoxybiphenyl in 10 mL methanol at ambient temperature under a nitrogen atmosphere was added 0.92 mL of 4.4M sodium methoxide in methanol solution (4 mmole). The mixture was stirred for 20 minutes and partitioned between Et$_2$O/ice-H$_2$O/2N HCl (aq.) and the organic phase separated, washed with saturated NaCl solution, and then ice-H$_2$O/saturated NaHCO$_3$ (aq) solution, dried over Na$_2$SO$_4$, filtered, and evaporated. The product was dried in vacuo to give 1.05 g of crude 3-bromo-4'-hydroxybiphenyl which was used without further purification.

EXAMPLE 20

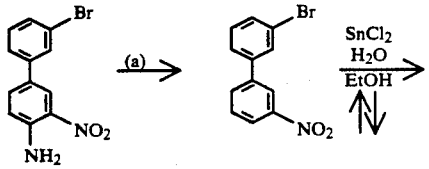

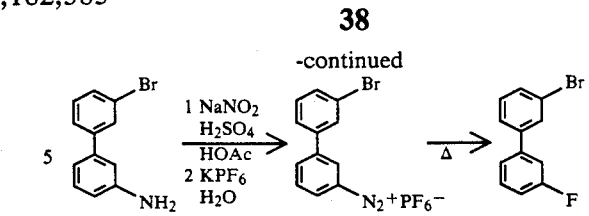

Step (a)

To a stirred solution of 816 μL (6.2 mmole) of 90% t-butylnitrite in 15 ml of DMF at 65° C. under nitrogen atmosphere was added dropwise, a solution of 905 mg (3.1 mmole) 3-bromo-3'-nitro-4'-aminobiphenyl [C.Dell'Erba, G. Garbarino, and G. Guanti, *Tetrahedron*, 27. 113 (1971)] in 10 mL DMF over a period of 6 minutes. The mixture was stirred further as above for 8 minutes.

The cooled mixture was partitioned between Et$_2$O-/ice-H$_2$O and the organic phase separated, washed twice with ice-H$_2$O, then with saturated NaCl solution, dried over Na$_2$SO$_4$, filtered, and evaporated.

The residue was purified by florisil chromatography with CH$_2$Cl$_2$-petroleum ether solvent to give a quantitative yield of 3-bromo-3'-nitrobiphenyl; NMR (CDCl$_3$) δ: 7.32–8.46 (m, Ar-H).

Using the analogous procedure outlined in Exs. 10, 11 and 12, 3-bromo-3'-fluorobiphenyl was obtained.

EXAMPLE 21

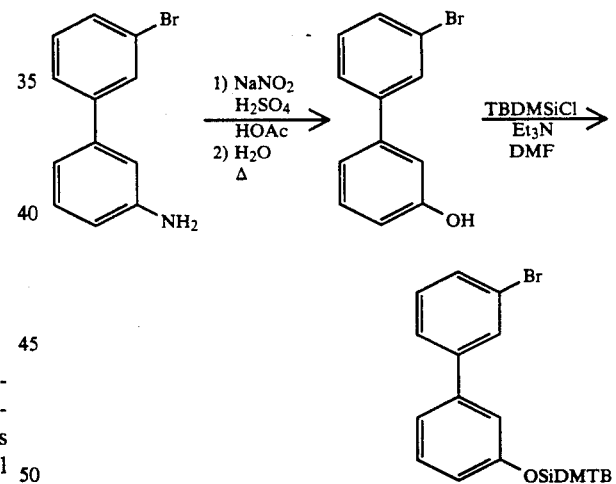

In a fashion analogous to the procedures outlined in Examples 13–15, the 3-bromo-3'-aminobiphenyl from Example 20 was converted into 3-bromo-3'-t-butyldimethylsiloxybiphenyl.

EXAMPLE 22

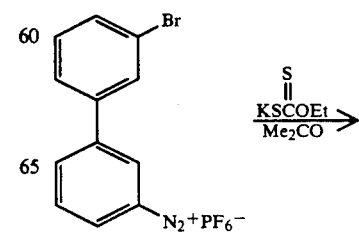

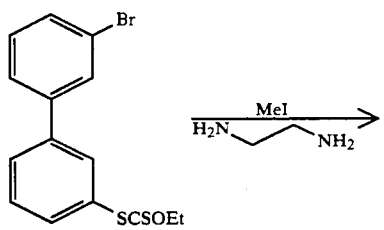

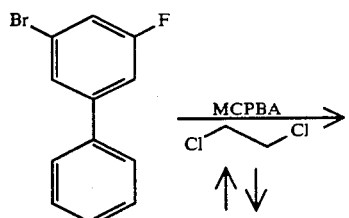

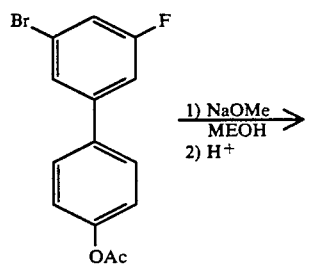

Utilizing the procedures previously outlined, the diazonium salt of Example 20 was converted to 3-bromo-3'-methylthiobiphenyl.

EXAMPLE 23

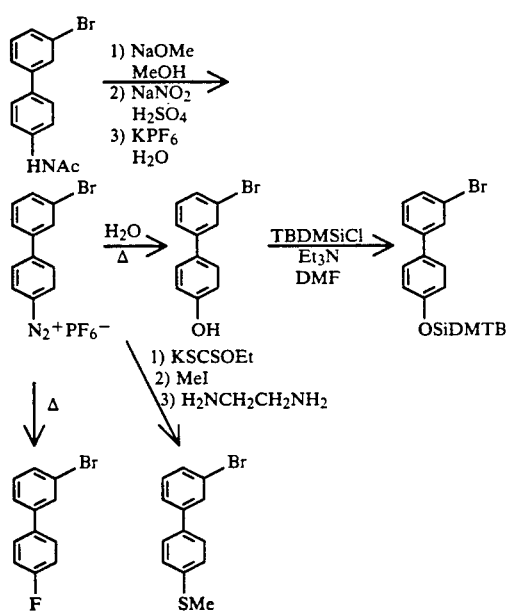

3-bromo-4'-acetamidobiphenyl was prepared according to the method of C. Dell 'Erba, et al., *Tetrahedron*, 27 113 (1971), and converted into the three 3-bromo-4'-substituted biphenyl derivatives depicted above utilizing the previously detailed procedures.

EXAMPLE 24

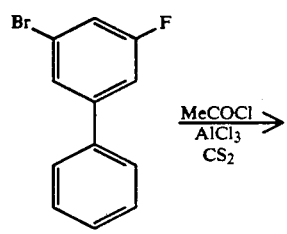

3-bromo-5-fluoro-4'-t-butyldimethylsilyloxybiphenyl was prepared in four steps utilizing the procedures previously detailed.

EXAMPLE 25

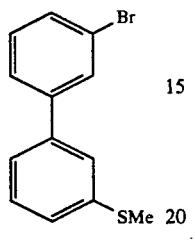

3-bromo-5-fluoro-4'-t-butyldimethylsilyloxymethyl-biphenyl was synthesized as outlined above employing the previously described procedures.

EXAMPLE 26
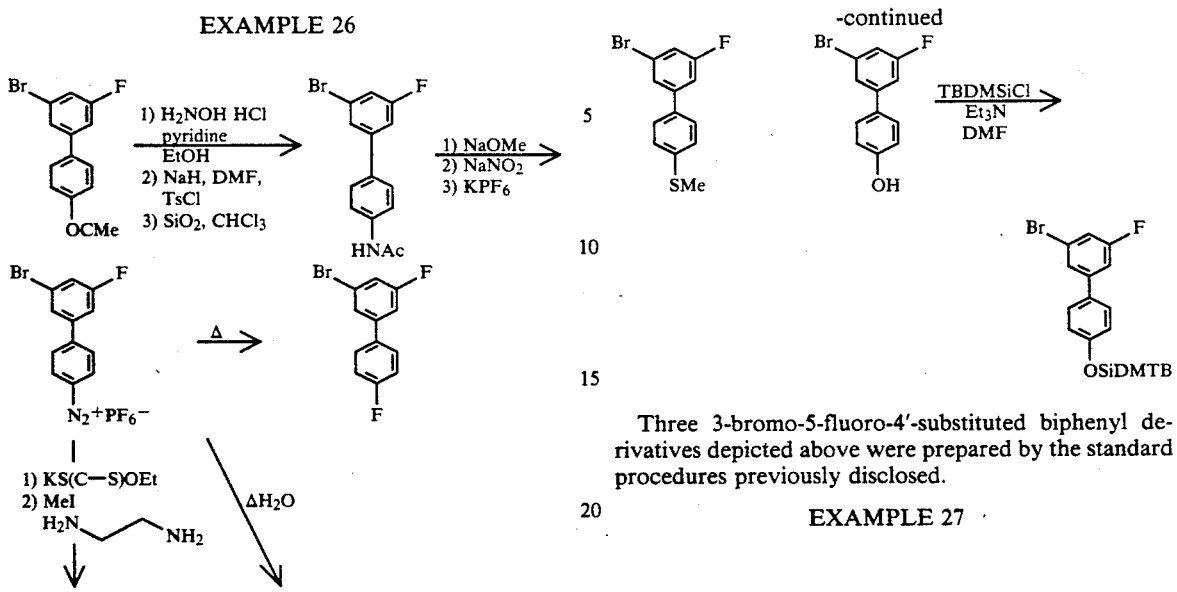
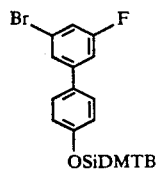
Three 3-bromo-5-fluoro-4'-substituted biphenyl derivatives depicted above were prepared by the standard procedures previously disclosed.
EXAMPLE 27
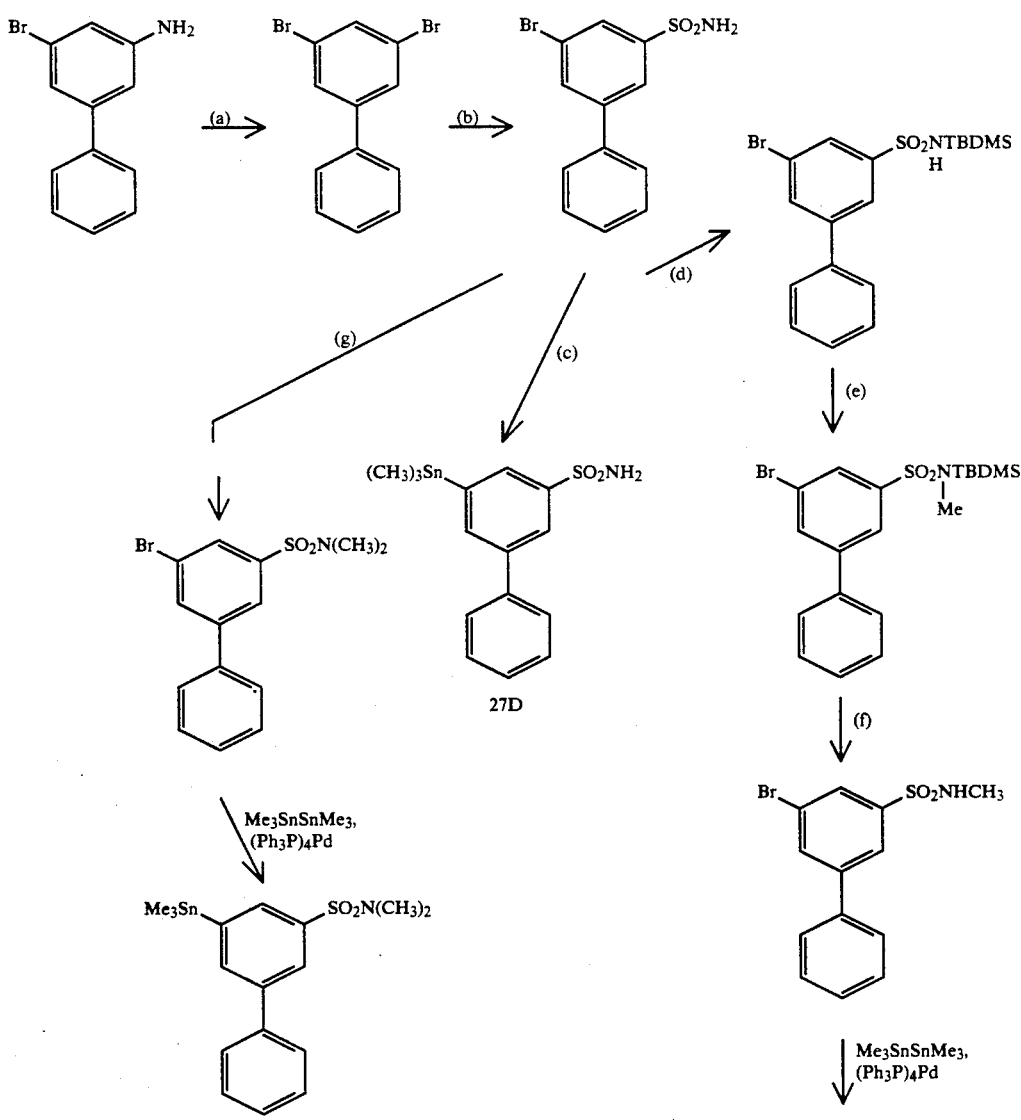

Step(a)

To a stirred solution of sodium nitrite (4.4 g; 63.9 mmol) in 44.3 ml of sulfuric acid in an ice-water bath was added a solution of 3-amino-5-bromobiphenyl (15.0 g, 60.1 mmol) in 176.7 ml glacial acetic acid over 30 minutes. The solution was stirred an additional 10 minutes. To a stirred solution of copper(I)bromide (9.5 g, 66.3 mmol) in 78.6 ml of 48% HBr at R.T. was added the above diazonium salt solution and the reaction mixture was stirred for 45 minutes under an inert atmosphere of nitrogen. The reaction appeared complete by TLC (petroleum ether). The reaction was quenched by the addition of a 1.5 L 5N NaOH-ice solution and the aqueous portion (pH 6.5) was extracted with 2.0 L ether. The ether extract was washed three times with brine and the solvent was removed in vacuo to provide 18.6 g of a brown oil. The crude material was purified by flash chromatography on silica gel eluting with hexanes. The higher $R_f$ product gave 15.6 g (83.1%) of 3,5-dibromobiphenyl and the lower $R_f$ by product gave 0.7 g of 3-bromobiphenyl. $^1$H NMR (300 MHz, CDCl$_3$, ppm): δ 7.36–7.54 (m,5H); 7.6–7.68 (m,3H).

Step(b)

To a stirred solution of 3,5-dibromo-biphenyl (0.5 g, 1.60 mmol), in 5 ml dry THF under N$_2$ atmosphere at −78° C., was added 0.67 ml of 2.5M n-butyllithium (1.68 mmol). A clear yellow solution resulted. After stirring 5 minutes, a solution of SO$_2$(g) (0.12 g) in 1.0 ml THF was added via syringe; TLC indicated nearly complete reaction. To the stirred reaction mixture was added 2,4,6-triisopropylbenzenesulfonylhydroxylamine (0.57 g, 2.0 mmol) and it was stirred for 15 minutes. The reaction appeared incomplete by TLC, and additional aminating agent (45.3 mg, 0.1 mmol) was added and the reaction stirred 15 minutes. This process was repeated and then the reaction mixture was partitioned between ethyl acetate/ice/water; the organic layer was separated and washed three times with 10 ml H$_2$O, and three times with 10 ml brine. The organic layer dried over MgSO$_4$, filtered and the solvent removed in vacuo, to give 1.0 g crude of product. The residue was purified by plate-layer chromatography eluted with dichloromethane-ethyl acetate (30:1) to give 300 mg (60%).
$^1$H NMR (200 MHz, DMSO, ppm): δ 7.47–7.59 (m, 3H), 7.71–7.78 (m, 2H), 7.95 (m, 1H), 8.08–8.13 (m, 2H).
IR: (nujol) 3370, 3275 cm$^{-1}$.
MS: (m/e) 313,311 (M+).

Step(c)

A mixture of 3-bromo-5-sulfonylbiphenyl (0.11 g, 0.36 mmole), Pd(PPh$_3$)$_4$ (8.4 mg, 7.3 μmol) and triphenylphosphine (1.0 mg, 3.8 μmol) in 1.33 mL toluene was stirred and degassed with a nitrogen purge. A solution of hexamethylditin (130.8 mg, 0.40 mmol) in 0.30 μL toluene was added via syringe and the solution was refluxed under N$_2$ for 2h. The cooled reaction mixture was partitioned between ethyl acetate/ice/water/aq. NaHCO$_3$. The organic layer was separated and washed three times with 10 ml of cold (0° C.) 10% aq. NaHCO$_3$ solution and twice with 10 ml brine; dried over MgSO$_4$, filtered and concentrated in vacuo. The crude product, a yellow-orange oil was purified by chromatography on silica gel plates (2000μ) eluted with 30:1 CH$_2$Cl$_2$: EtOAc to give 95 mg (66.1%), as a white foam.
$^1$H NMR (300 MHz, CDCl$_3$, ppm): δ 0.38 (s, 9H), 4.96 (bs, 2H), 7.35–7.48 (m, 3H), 7.55–7.59 (m, 2H), 7.85 (m, 1H), 8.0 (m, 1H), 8.06 (m, 1H).
IR: (CH$_2$Cl$_2$) 3430, 3335 cm$^{-1}$.

Step (d)

A stirred mixture of the sulfonamide (25 mg, 0.08 mmol), t-butyldimethylsilyl chloride (0.60 mg, 4.0 μmol), and N-tert-butyldimethylsilyl)-N-trifluoromethylacetamide (20.7 μL, 88 μmol) in 0.5 ml MeCN was refluxed for 2 hours under N$_2$ atmosphere. The cooled reaction mixture was partitioned between EtOAc/ice/water/aq. NaHCO$_3$. The organic layer was separated and washed three times with 10 mL dilute aq. NaHCO$_3$ solution and three times with 10 mL brine; dried over MgSO$_4$; filtered and concentrated in vacuo to give 27 mg of crude product. It was chromatographed on a silica gel plate (1000μ) eluted with 9:1 CH$_2$Cl$_2$: hexane to give 24 mg (70.3%) of product.
$^1$H NMR (200 MHz, CDCl$_3$, ppm): δ 0.28 (s, 6H), 0.94 (s, 9H); 4.46 (bs, 1H); 7.43–7.60 (m, 5H), 7.89 (m, 1H), 7.99 (m, 1H), 8.03 (m, 1H).

Step (e)

To a stirred solution of the silylated sulfonamide (42.7 mg, 0.1 mmol) in 0.43 ml DMF was added 4.3 mg (0.11 mmol) of a 61.1% mineral oil dispersion of NaH. The mixture was stirred under N$_2$ at ambient temperature for 1 hr. To the stirred mixture was added neat methyliodide (29.8 mg, 0.21 mmol) and stirred further for 3 hours; followed the reaction by TLC (1:1 hexane: dichloromethane). The reaction mixture was partitioned between ethyl acetate/ice and water, and the organic layer separated, washed three times with 20 mL deionized water and three times with 20 mL brine; then dried over MgSO$_4$, filtered and concentrated in vacuo. The crude product (44.0 mg) was chromatographed on a silica gel plate (1000μ) eluted with 1:1 hexane: dichloromethane to give 32.0 mg (78.1%) purified product.
$^1$H NMR (200 MHz, CDCl$_3$, ppm): δ 0.38 (s, 6H), 1.07 (s, 9H), 2.80 (s, 3H), 7.44–7.62 (m, 5H), 7.92 (m, 2H), 7.97 (m, 1H).

Step(f)

To a stirred solution of 3-bromo-5-N-t-butyldimethylsilyl-N-methylsulfonamidobiphenyl (32.0 mg, 73.0 μmol) in 0.32 ml anhydrous THF at 0° C. under N$_2$ was added sequentially 12.5 μl (0.22 mmol) glacial acetic acid and then a 1M solution of tetrabutylammonium fluoride (80.3 μl, 80.3 μmol) in the THF. The mixture was stirred at 0° C. for 0.5 hr. The reaction mixture was partitioned between EtOAc/ice-water, the organic layer was separated and washed three times with saturated sodium bicarbonate solution, three times with 10 mL water and three times with 10 mL brine, then dried over Na₂SO₄, filtered and the solvent removed in vacuo to give 28 mg of crude product. The mixture was chromatographed on a 1000μ silica gel plate eluting with 9:1 dichloromethane: hexane to give 24 mg (84%) the desired N-methyl sulfonamide.

¹H NMR (200 MHz, CDCl₃, ppm): δ 2.75 (d, 3H), 4.4 (bm, 1H), 7.45–7.61 (m, 5H), 7.96 (m, 1H), 7.98 (m, 1H), 8.0 (m, 1H).

Using the procedures disclosed in step(c), this material was converted into the analogous trimethylstannyl derivative.

Step(g)

To a stirred solution of the sulfonamide (0.2 g, 641 μmol) in 2 ml DMF was added 52.6 mg (1.34 mmol) 61.1% of a mineral oil dispersion of NaH and the reaction stirred 1 hour at room temperature until gas evolution is complete. To the stirred mixture at 0° C. was added neat methyliodide (0.17 mL), and the solution stirred 30 minutes; TLC (1:1 CH₂Cl₂: hexane) indicated complete reaction. The reaction mixture was partitioned between ethyl acetate and ice-water, and the organic extract separated, washed three times with 50 mL brine, dried over Na₂SO₄, filtered and concentrated in vacuo to give 250 mg of crude product. It was chromatographed on two 2000μ silica gel plates eluted with 1:1 hexane: dichloromethane to give 201 mg(92.2%) the desired product. ¹H NMR (200 MHz, CDCl₃, ppm): δ 2.8 (s, 6H), 7.46–7.62 (m, 5H), 7.91 (m, 2H), 7.96 (m, 1H).

Using the procedure described in step(c), this biphenyl derivative was converted to the analogous trimethylstannyl derivative.

EXAMPLE 28

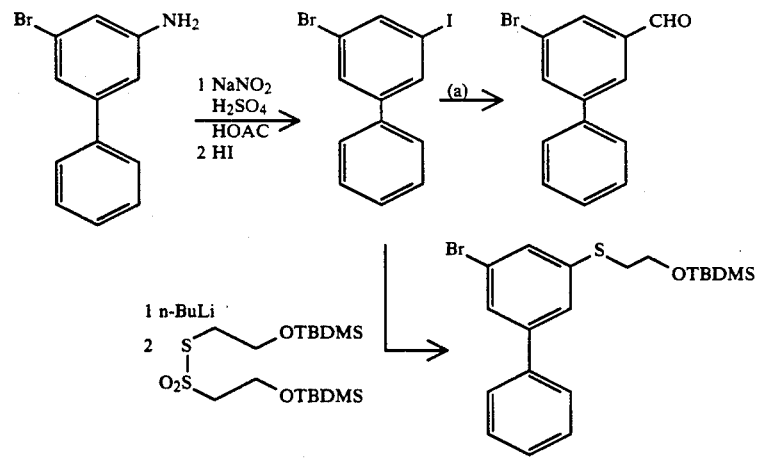

Step (a)

To a stirred solution of 3-bromo-5-iodobiphenyl (5.5 g, 15.4 mmol) in 70 mL dry THF at −78° C. under N₂ atmosphere was added dropwise a 2.5M solution of n-butyllithium in hexanes (6.4 mL, 16.1 mmol) over 5 minutes. The mixture was stirred 10 minutes and anhydrous DMF (2.4 mL, 30.7 mmol) was quickly added. After 15 minutes the reaction was quenched by the addition of saturated ammonium chloride solution and warmed to room temperature. The reaction mixture was partitioned between diethyl ether and water, the organic extract washed with brine, dried over MgSO₄, filtered and concentrated in vacuo. The crude product (4.37 g), as a yellow oil, was chromatographed on silica gel eluted with a gradient of 0–3% ethyl acetate in hexane to provide. 3.61 g. (90%) of purified product, as an opaque oil. ¹H NMR (200 MHz, CDCl₃, ppm): δ 7.4–8.04 (m, 8H), 10.04 (s, 1H);

IR: (CH₂Cl₂): 1700 cm⁻¹.

MS: m/e 262,260 (M+).

EXAMPLE 29

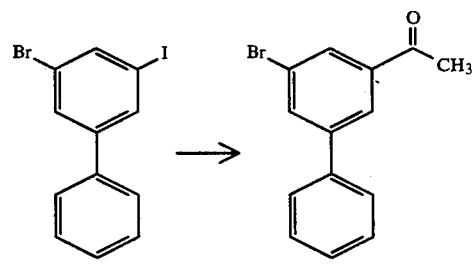

To a stirred solution of 3-bromo-5-iodobiphenyl (0.5 g, 1.4 mmol) in 5 mL dry THF at −70° C. under N₂ atmosphere was added a 2.5M solution of n-butyllithium in hexanes (0.58 mL, 1.47 mmol). The mixture was stirred 10 minutes, and a 0.2M solution of magnesium bromide (14 mL, 2.8 mmol) in THF was added. The reaction was warmed to −23° C. in a dry ice-CCl₄ bath. After 15 minutes at −23° C., neat 2-acetylthiopyridine (178 μl, 1.40 mmol) was added and the reaction was monitored by TLC. The 2-acetylthiopyridine was completely consumed after 10 minutes however, starting material remained, and an additional 50 μl of 2-acetylthiopyridine was added. The reaction mixture was warmed to room temperature and quenched with 3 mL of 1M aqueous NH₄Cl and then partitioned between ethylacetate and cold water. The organic layer was separated and washed with cold 2N NaOH and brine, then dried over MgSO₄, filtered and concentrated in vacuo to give 486 mg of crude material. It was chromatographed on two 2000μ silica gel plates eluted with 9:1 hexane:ethylacetate to give 202 mg (52%), as a crystalline solid.

¹H NMR (200 MHz, CDCl₃, ppm): δ 2.64 (s, 3H), 7.4–8.1 (m, 8H);

IR (CH₂Cl₂): 1690 cm⁻¹.

EXAMPLE 30

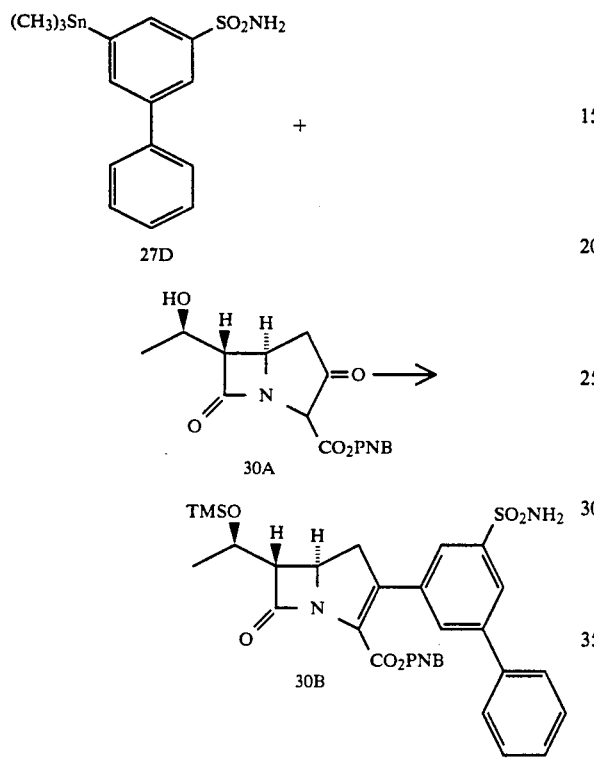

To a dry flask charged with the bicyclic ketoester carbapenem derivative (58.4 mg, 0.168 mmol) and purged with N₂ was added 1.0 mL dry THF. The solution was chilled to −78° C. and diisopropylamine (25.8 μL, 0.184 mmol) was added. The reaction was stirred 10 minutes and became a clear yellow solution, then trifluoromethanesulfonic anhydride (30.6 μL, 0.184 mmol) was added and stirring continued at −78° C. for 15 minutes. To the reaction mixture was added neat triethylamine (25.4 μL, 184 μmol) and trimethylsilyl trifluoromethanesulfonate (35.6 mL, 184 μmol) and continued stirring for 20 minutes.

The arylstannane sulfonamide (73.0 mg, 0.18 mmol), Pd₂(dba)₃·CHCl₃ (3.47 mg, 3.4 μmol) and tris (2,4,6-trimethoxyphenyl)phosphine (7.11 mg, 13.5 μmol) were added all at one after the addition of 0.83 mL N-methylpyrolidinone. Finally, a solution of 1.5M zinc chloride in diethyl ether (276 μl, 0.184 mmol) was added, and the reaction mixture was allowed to warm with the aid of a warm water bath for an additional 20 minutes during which time a wine red color developed. The reaction mixture was partitioned between ethyl acetate/ice and aqueous. NaHCO₃ mixture and the organic layer was separated and washed three times with 10 mL cold dilute NaHCO₃ and three times with 10 ml brine; dried over MgSO₄, filtered, and concentrated in vacuo. Chromatographed crude product on one 1000μ silica gel plate eluted with 2:3 hexane:ethyl acetate to give 70.2 mg (61.0%) of product.

¹H NMR (300 MHz, CDCl₃, ppm): δ 0.12 (s, 9H), 1.25 (d, 3H), 3.19–3.41 (m 3H), 4.21–4.32 (m, 2H) 5.15 (d, 1H), 5.25 (d, 1H), 7.24–8.11 (m, 12H).

EXAMPLE 31

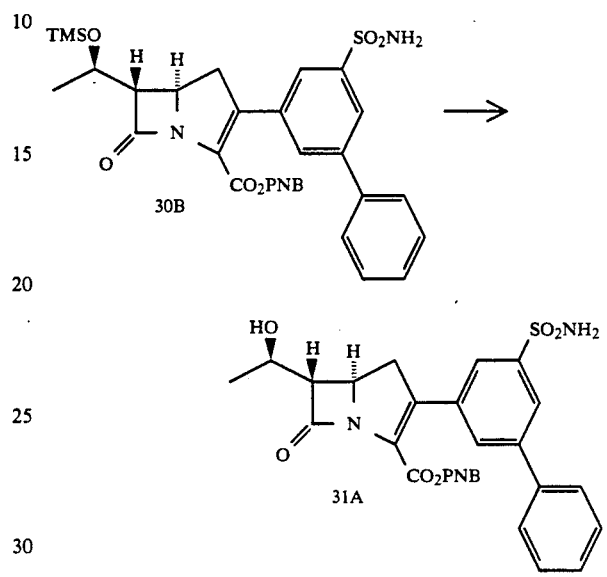

To a stirred solution of the silyl ether (67.0 mg, 0.107 mmol) in 1 mL dry THF at 0° C. was added glacial acetic acid (18.3 μl 0.321 mmol) and a solution of 1M tetrabutylammoniumfluoride in THF (107 μl, 0.107 mmol). The reaction mixture was stirred 10 minutes and then partitioned between EtOAc/ice/water/dilute aq. NaHCO₃. The organic layer was separated and washed three times with 10 mL saturated NaHCO₃ solution and three times with 10 mL brine, then dried over MgSO₄, filtered and concentrated in vacuo. The crude product (55.0 mg), a yellow foam, was chromatographed on a 1000μ silica gel plate eluting with 7:3 hexane:ethyl acetate to give the purified product 35.0 mg (59.2%). ¹H NMR (300 MHz, d₆-Me₂CO, ppm)δ: 1.32 (d, 3H), 3.38 (dd, 1H), 3.52 (dd, 1H), 3.7 (dd, 1H), 4.2 (m, 1H), 4.45 (m, 1H), 5.35 (ABq, 2H), 6.75 (bs, 2H) 7.4–7.7 (m, 5H), 7.94 (m, 1H), 8.15 (m, 2H); IR (CH₂Cl₂): 1775, 1725 cm⁻¹; UV (dioxane, λmax): 310 nm (sh), 259 nm.

EXAMPLE 32

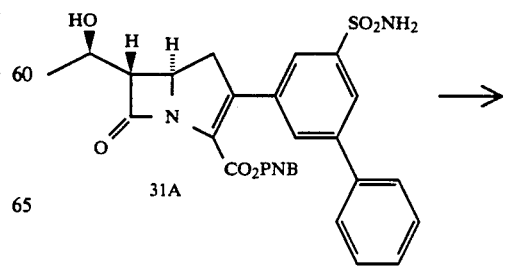

-continued

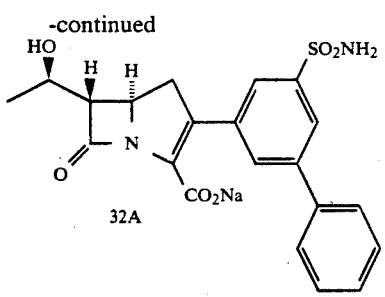

32A

A mixture in 0.5 mL dry THF of p-nitrobenzyl ester (35.0 mg, 63.5 μmol), 3.5 mg 10% Pd/C, and NaHCO₃ (6.0 mg) was hydrogenated at 50 psi and ambient temperature for 15 minutes. After this time an additional 3.5 mg 10% Pd/C was added and the hydrogenation continued for 30 minutes at 50 psi. The reaction mixture was filtered through a celite pad to give a clear filtrate, which was concentrated in vacuo. The solid residue was dissolved in deionized H₂O and chromatographed on a 1000μ reverse phase silica gel plate eluted with 5:1 water: acetonitrile in a chilled developing chamber. The product 14.5 mg (50.5%) was isolated as a white fluffy solid, after lyophilization. $^1$H NMR (300 MHz, D₂O, ppm) δ: 1.24 (d, 3H), 3.18 (m, 1H), 3.56 (m, 1H), 3.64 (m, 1H), 4.38 (m, 2H), 7.5-7.82 (m, 5H), 7.87 (m, 2H), 8.08 (bs, 1H); IR (nujol): 1750, 1595 cm⁻¹; UV (H₂O, λmax): 303, 254 nm.

EXAMPLE 33

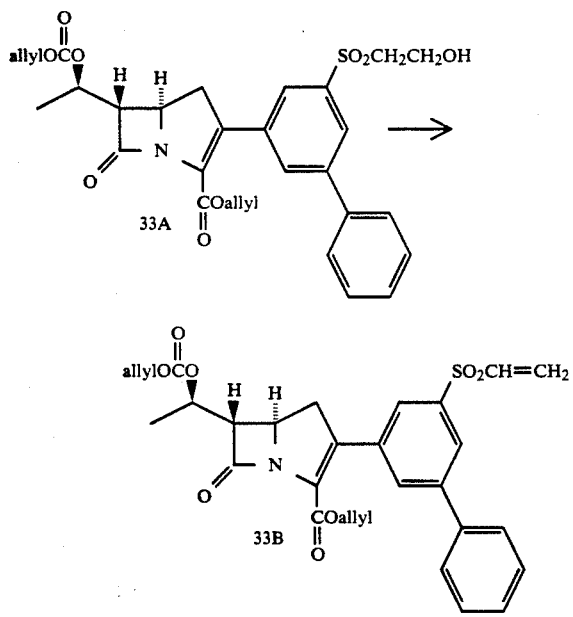

To a stirred solution of the carbapenem derivative (60 mg, 0.103 mmol) in 0.6 mL dry acetonitrile at 0° C. under N₂ atmosphere was added neat N-methylimidazole (17.2 μl, 0.216 mmol) and trifluoromethanesulfonic anhydride (18.2 μl, 0.108 mmol). The progress of the reaction was followed by TLC. After 15 minutes, the TLC indicated the complete disappearance of starting material. The reaction mixture was concentrated in vacuo. The 200 MHz NMR indicated a mixture of vinyl sulfone and the imidazolium adduct. The crude product was dissolved in dichloromethane, transferred into a 15 ml centrifuge tube, concentrated to a 1.0 mL volume and the imidazolium adduct precipitated by the addition of diethyl ether. After centrifuging the ether was decanted off, and evaporated to yield 32 mg (55%) of the vinyl sulfone product as a white foam.

$^1$H NMR (200 MHz, CDCl₃, ppm) δ: 1.52 (d, 3H), 3.31-3.39 (m, 2H), 3.46-3.51 (dd, 1H), 4.31-4.41 (dt, 1H), 4.65-4.74 (m, 4H), 5.16-5.44 (m, 5H), 5.79-6.04 (m, 2H), 6.1 (d, 1H), 6.52 (d, 1H), 6.66 (dd, 1H), 7.4-7.63 (m, 5H), 7.83-7.87 (m, 2H), 8.06 (m, 1H).

EXAMPLE 34

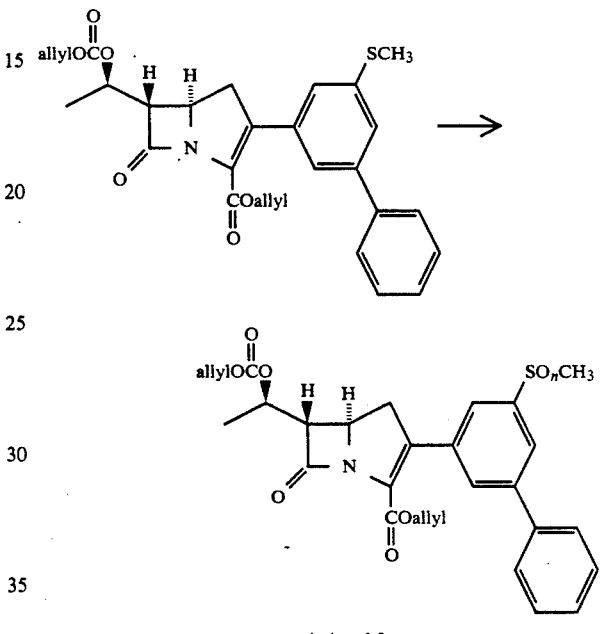

n is 1 and 2

To a stirred solution of 2-(5'-methylthio-3'-biphenyl)-carbapenem (41.1 mg, 79.2 μmol) in 1 mL dichloromethane at 0° C. under a N₂ atmosphere was added 0.5M aqueous NaHCO₃ (0.5 mL) and MCPBA (19.1 mg, 0.11 mmol). The reaction was stirred 25 minutes at 0° C.; at 10 minutes the TLC indicated the complete consumption of the methyl sulfide and the presence of two new spots. The reaction was quenched with 0.5M aqueous Na₂S₂O₃ solution and partitioned between EtOAc/ice/water. The organic phase was separated and washed with brine, dried over Na₂SO₄, filtered and concentrated in vacuo to give 46.2 mg of crude product mixture, a clear film. It was chromatographed on a 1000μ silica gel plate eluting with 15% EtOAc in dichloromethane to give 9.3 (21.3%) of sulfone, as the more mobile component; and 25.8 mg (60.9%) of sulfoxide, as the less mobile component.

Sulfoxide:
$^1$H NMR: (300 MHz, CDCl₃, ppm) δ: 1.48 (d, 3H), 2.77 (s, 3H), 3.25-3.36 (m, 2H), 3.44 (dd, 1H), 4.33 (td, 1H), 4.59-4.72 (m, 4H), 5.13-5.39 (m, 5H), 5.78-5.97 (m, 2H), 7.24-7.79 (m, 8H); IR: (CH₂Cl₂) 1772, 1745, 1720 cm⁻¹; UV: (dioxane) λmax 314,258 nm.

Sulfone:
$^1$H NMR: (300 MHz, CDCl₃, ppm) δ; 1.48 (d, 3H), 3.09 (s, 3H), 3.26-3.36 (m, 2H), 3.45 (dd, 1H), 4.33 (td, 1H), 4.61-4.71 (m, 4H), 5.14-5.39 (m, 5H), 5.79-5.92 (m, 2H), 7.24-8.09 (m, 8H); IR: (CH₂Cl₂) 1775, 1745, 1722 cm⁻¹; UV: (dioxane) λmax 312,257 nm.

EXAMPLE 35

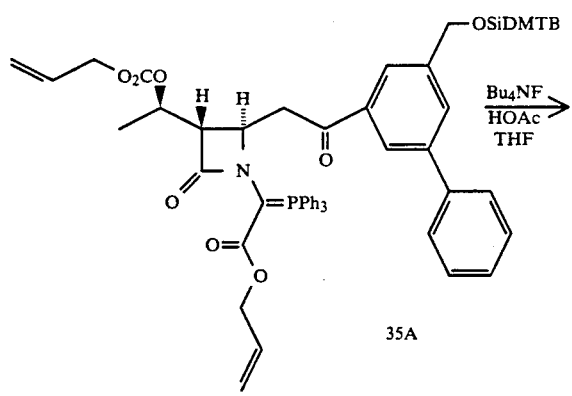

35A

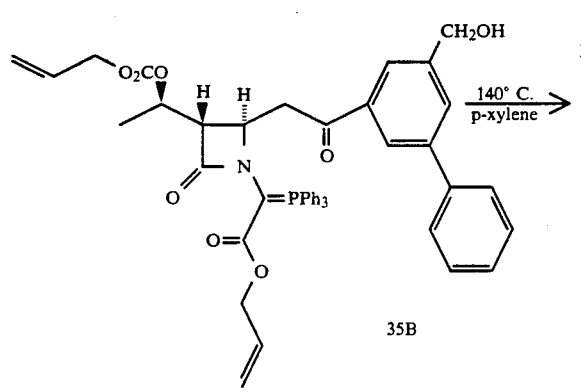

35B

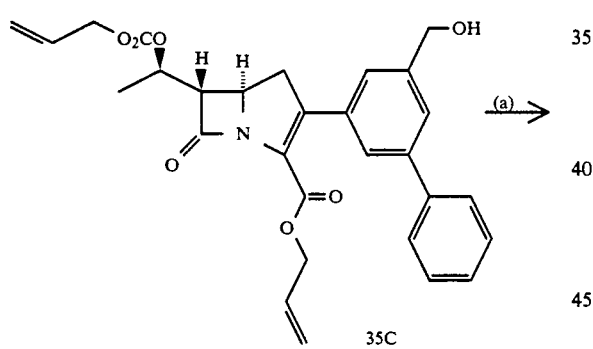

35C

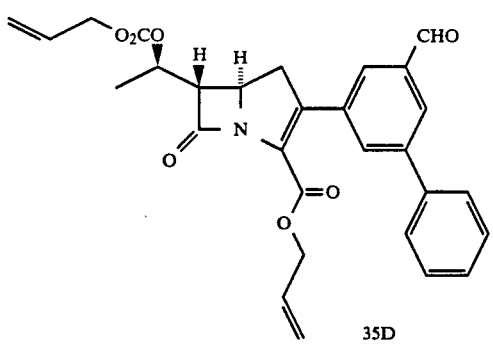

35D

Step (a)

To a stirred solution of 65.3 mg (0.13 mmole) of carbapenem biphenyl carbinol derivative in 1.6 mL sieve dried $CH_2Cl_2$ at ambient temperature was added sequentially 17 mg of powdered 3 Å sieves and 27 mg (0.23 mmole) of N-methylmorpholine-N-oxide. The yellow solution was stirred for 5 minutes and then 9.1 mg (0.26 mmole) of tetrapropylammonium perruthenate was added. The resulting mixture was stirred 5 minutes and then quickly filtered through a layer of silica gel with $CH_2Cl_2$—EtOAc (1:1) solvent. The filtrate was rotoevaporated and dried in vacuo to give 51.9 mg (80%) of oxidized product; NMR ($CDCl_3$) δ: 1.5 (d, $CH_3$), 3.34 (m, 2H-1). 3.46 (dd, 1H-6), 4.34 (td, 1H-5), 4.34 (m, 2—$OCH_2CH=CH_2$), 5.24 (m, 1H-8 and 2—$CH=CH_2$), 5.88 (m, 2—$CH=CH_2$), 7.46 (m, 3Ar—H), 7.6 (d, 2Ar—H), 7.82 (s, 1Ar—H), 7.84 (s, 1Ar—H), 8.05 (s, 1Ar—H), and 10.1 (s, CHO).

EXAMPLE 36

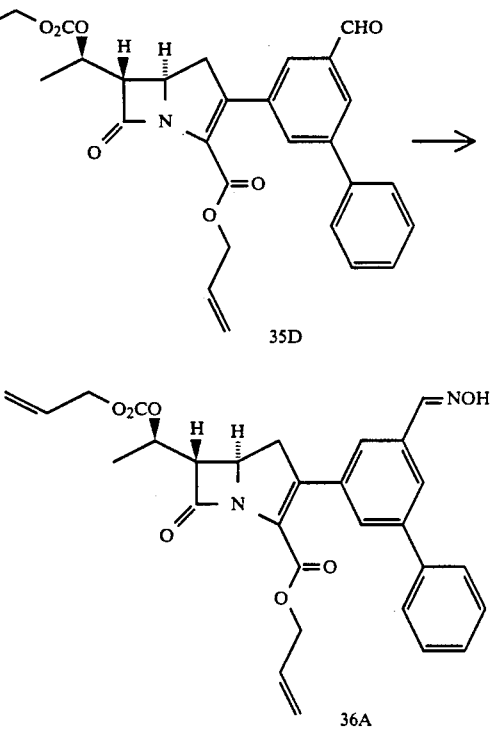

35D

36A

To a stirred solution of 51.9 mg (0.1 mmole) of carbapenem biphenyl carboxaldehyde derivative from Example 35 in 0.7 mL absolute ethanol and 0.7 mL pyridine at 0° C. under a nitrogen atmosphere was added 7.2 mg (0.1 mmole) of neat hydroxylamine hydrochloride. The mixture was stirred at 0° C. for 5 minutes and then partitioned between EtOAc/ice/saturated $NH_4Cl$ (aq.) solution and the organic phase separated. It was washed successively with ice/saturated $NaHCO_3$ (aq.) solution, $H_2O$, and brine, then dried over $Na_2SO_4$, filtered, and evaporated.

The crude oxime was immediately employed in the next transformation but maybe purified by PLC to give pure material; IR ($CH_2Cl_2$): 3560, 1780, 1745, and 1720 $cm^{-1}$; NMR ($CDCl_3$) δ: 1.52 (d, $CH_3$), 1.6 (bs, OH), 3.32 (m, 2H-1), 3.46 (dd, 1H-6), 4.34 (dt, 1H-5), 4.68 (m, 2—$OCH_2CH=CH_2$), 5.24 (m, 1H-8 and 2—$CH=CH_2$), 5.84 (m, 2—$CH=CH_2$), 7.36–7.78 (m, Ar-H), and 8.2 (s, CH=NO).

EXAMPLE 37

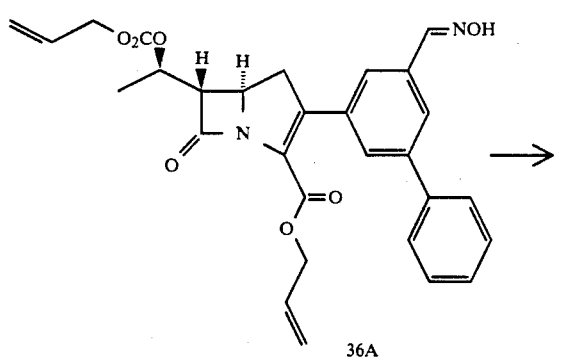

36A

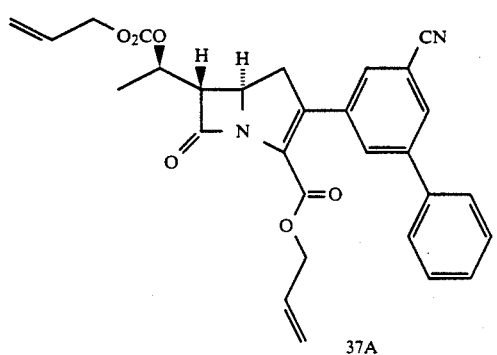

37A

To a stirred solution of 53.1 mg (0.1 mmole) of crude oxime from Example 36 in 1.6 mL of sieve dried CH$_2$Cl$_2$ at −78° C. under a nitrogen atmosphere was added sequentially 21.9 mg (0.22 mmole) of neat triethylamine and 29.1 mg (0.1 mmole) of neat triflic anhydride. After stirring 15 minutes at −78° C., an additional 13.4 mg (0.05 mmole) of triflic anhydride was added and the mixture stirred further for 15 minutes.

The mixture was partitioned between EtOAc/ice/-saturated NH$_4$Cl (aq.) solution and the organic phase was separated, washed with saturated NaHCO$_3$ (aq.) solution/ice and then brine, dried over Na$_2$SO$_4$, filtered, and evaporated.

The residue was purified by PLC [one development 5% EtOAc in CH$_2$Cl$_2$] to give 24.3 mg (47%) of biphenylnitrile carbapenem derivative; IR (CH$_2$Cl$_2$) 2235, 1780, 1745, and 1720 cm$^{-1}$; NMR (CDCl$_3$) δ: 1.5 (d, CH$_3$), 3.29 (m, 2H-1), 3.46 (dd, 1H-6), 4.34 (td, 1H-5), 4.66 (m, 2—OCH$_2$CH=CH$_2$), 5.26 (m, 1H-8 and 2—CH=CH$_2$), 5.88 (m, 2CH=CH$_2$), 7.38–7.83 (m, Ar-H).

EXAMPLE 38

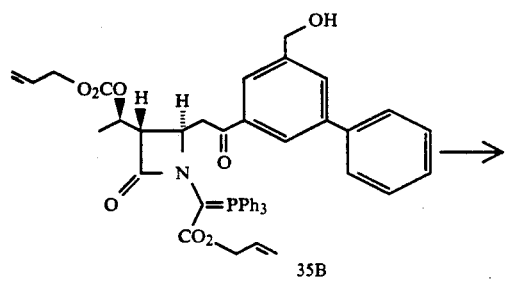

35B

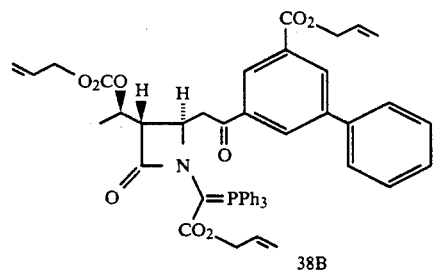

38B

To a stirred solution of 500 mg (0.65 mmole) of biphenylcarbinolazetidnonylphosphorane derivative in 10 mL acetone at 0° C. was added slowly 0.75 mL (2.0 mmole) of 2.67 M Jones reagent. The mixture was stirred 15 minutes at ice-H$_2$O bath temperature and 3 mL of saturated NaHSO$_3$ (aq.) solution added. The reaction solution was decanted and partitioned between EtOAc/ice/0.1M pH 7 phosphate buffer. The organic phase was separated, dried over Na$_2$SO$_4$, filtered, evaporated, and dried in vacuo to give 287 mg (57%) of crude acid dervivative; IR (CH$_2$Cl$_2$) 1743, 1690, and 1605 cm$^{-1}$.

To a stirred solution of 254 mg (0.32 mmole) of crude acid in 4 mL of DMF at ambient temperature was added 62 mg (0.48 mmole) of diisopropylethylamine and 58 mg (0.48 mmole) of allyl bromide. The resulting solution was stirred overnight at room temperature.

The reaction mixture was concentrated in vacuo and the concentrate partitioned between EtOAc and cold 1N HCl, and the organic phase separated, dried over Na$_2$SO$_4$, filtered, and evaporated.

The residue was purified by PLC [one development CH$_2$Cl$_2$-EtOAc (9:1)] to give (64%) of foamy ester product; IR (CH$_2$Cl$_2$) 1743, 1725 (sh), 1690, and 1610 cm$^{-1}$.

EXAMPLE 39

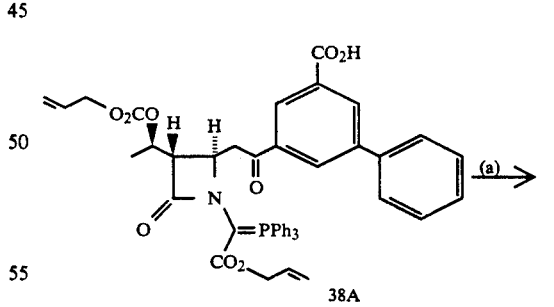

38A

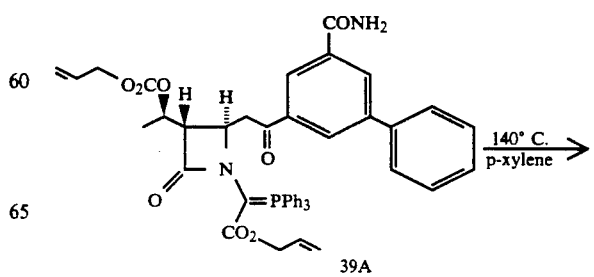

39A

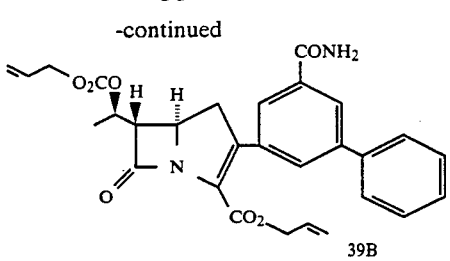

39B

Step (a)

To a stirred solution of 140 mg (0.18 mmole) of carboxylic acid derivative, prepared according to Example 38, in 4 mL THF at room temperature was added 45 mg (0.34 mmole) of neat 1-hydroxybenzotriazole and 44 mg (0.23 mmol) of 1-(3-dimethylaminopropyl)-3-ethyl-carbodiimide hydrochloride were added, and the mixture stirred 0.75 hours. After this time 2 mL of cold, saturated NH$_3$ in THF solution was added and the mixture stirred for 1.0 hour. The reaction mixture was concentrated and purified by column chromatography on silica gel to give the amide product; IR (CH$_2$Cl$_2$) 1743, 1680, and 1610 cm$^{-1}$.

EXAMPLE 40

Utilizing the procedure outlined in Example 39 and substituting MeOH for NH$_3$/THF, the corresponding methyl ester was prepared.

EXAMPLE 41

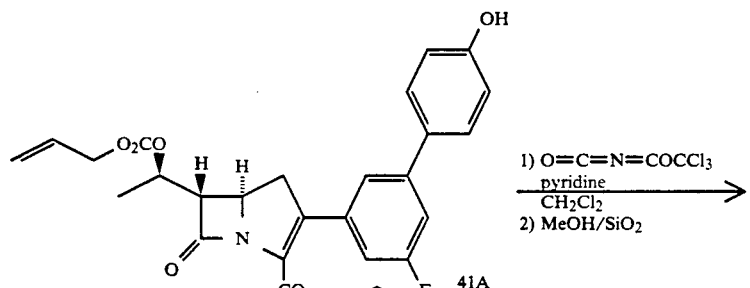

41A

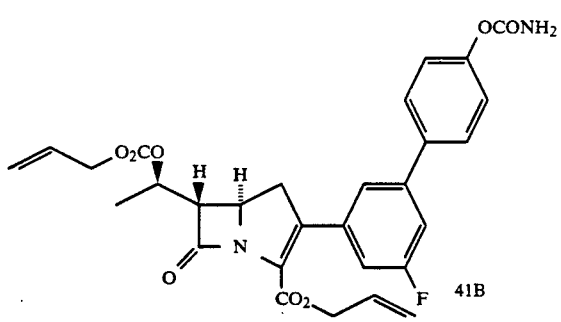

41B

To a stirred solution of 209.7 mg (0.4 mmol) of carbapenem derivative 41A in 3 mL of sieve dried methylene chloride at 0° C. under a nitrogen atmosphere was added sequentially 13.1 mg (0.165 mmol) of pyridine and then 117 mg (0.62 mmol) of trichloroacetylisocyanate. The resulting mixture was stirred at 0° C. for 40 minutes.

The reaction mixture was partitioned between ethylacetate, ice-H$_2$O, and 2N hydrochloric acid. The organic phase was separated, washed with saturated aqueous sodium chloride solution, dried over anhydrous sodium sulfate, filtered, evaporated, and dried in vacuo to give 313 mg of crude intermediate.

The intermediate was dissolved in 5 mL methanol cooled to 0° C. in an ice-H$_2$O bath, slurried with sufficient EM-60 silica gel and stirred further for 1 hour, and then aged overnight under refrigeration. The reaction mixture was filtered, washed with ether and the filtrate evaporated.

Purification by plate layer chromatography on two 1000 silica gel plates developed with methylene chloride-ether (6:1) provided 157.4 mg (69%) of 41B: IR (CH$_2$Cl$_2$): 3535, 3430, 1780, 1750, 1720 cm$^{-1}$; $^1$H NMR (200 MHz, CDCl$_3$, ppm): δ 1.53 (d, 3H), 3.16-3.40 (m, 2H), 3.44 (dd, 1H), 4.32 (dt, 1H), 4.66 (m, 4H), 5.06 (bs, 2H), 5.1-5.44 (m, 5H), 5.74-6.04 (m, 2H), 6.98-7.58, (m, 7H). UV (dioxane, λmax: 310, 277 nm.

EXAMPLE 42

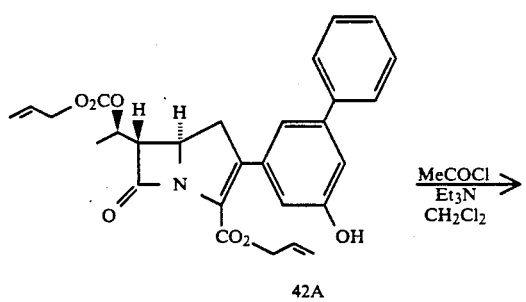

42A

-continued

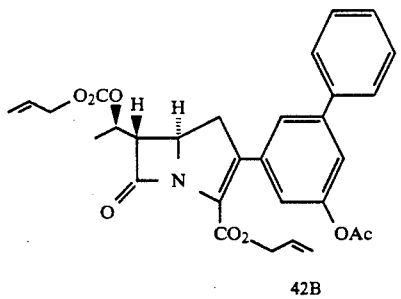

42B

To a stirred solution of 45.9 mg (0.08 mmol) of carbapenem derivative 42A in 2 mL sieve dried acetonitrile at 0° C. under a nitrogen atmosphere was added 17.7 μL (0.16 mmol) of triethylamine and then 8.4 μL (0.12 mmol) of acetyl chloride. The reaction mixture was stirred 25 min. at 0° C. and then partitioned between EtOAc/ice-H$_2$O. The organic phase was separated, washed with cold, saturated NaHCO$_3$ (aq) solution, then with saturated sodium chloride solution, dried over anhydrous Na$_2$SO$_4$, filtered, evaporated, and dried in vacuo to give a quantitative yield of acetoxyl derivative 42B; IR (CH$_2$Cl$_2$): 1780, 1745, 1722 cm$^{-1}$; $^1$H NMR (300 MHZ, CDCl$_3$, ppm): δ 1.48 (d, 3H), 2.3 (s, 3H), 3.18–3.36 (m, 2H), 3.41 (dd, 1H), 4.28 (td, 1H), 4.58–4.76 (m, 4H), 5.1–5.4 (m, 5H), 5.74–5.95 (m, 2H), 7.06–7.54 (m, 8H). UV (dioxane, λ$_{max}$: 320, 252 nm.

EXAMPLE 43

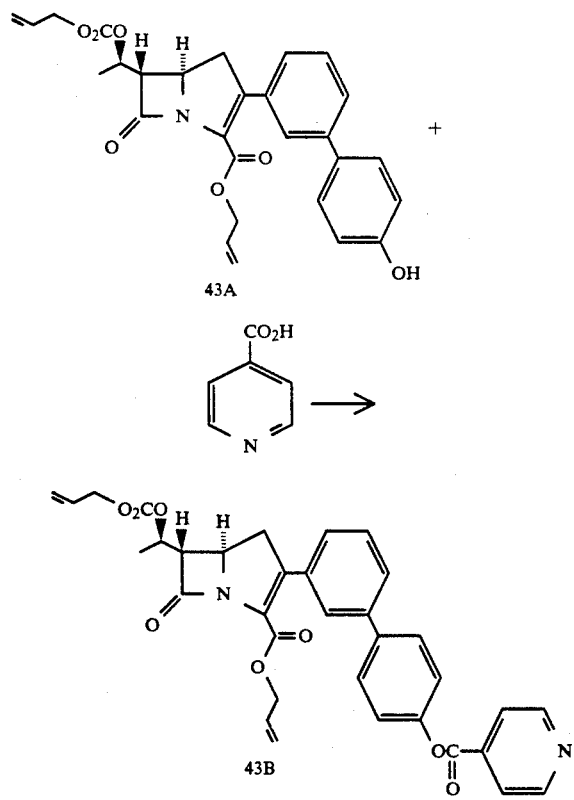

temperature for 0.75 hours. After this time, 60 mg (0.1 mmole) of neat hydroxybiphenyl carbapenem derivative was added and the resulting mixture stirred further for 17 hours.

The mixture was partitioned between EtOAc and ice-H$_2$O and the organic phase separated, washed with saturated NaCl solution, dried over Na$_2$SO$_4$, filtered, and evaporated.

The residue was purified by PLC [two developments CH$_2$Cl$_2$-EtOAc (4:1)] to give 17.1 mg (24%) of product; NMR (CDCl$_3$) δ: 1.5 (d, CH$_3$), 3.25 (m, 2H-1), 3.44 (dd, 1H-6), 4.32 (td, 1H-5), 4.68 (m, 2OCH$_2$CH=CH$_2$), 5.28 (m, 2CH=CH$_2$ and 1H-8), 5.9 (m, 2CH=CH$_2$), 7.28–7.68 (m, 8ArH), 8.04 (d, 2PyH), and 8.88 (d, 2PyH); IR(CH$_2$Cl$_2$): 1780, 1745, and 1725 cm$^{-1}$; UV:- λ$_{max}^{dioxane}$ 255 nm, 300 nm (sh).

EXAMPLE 44

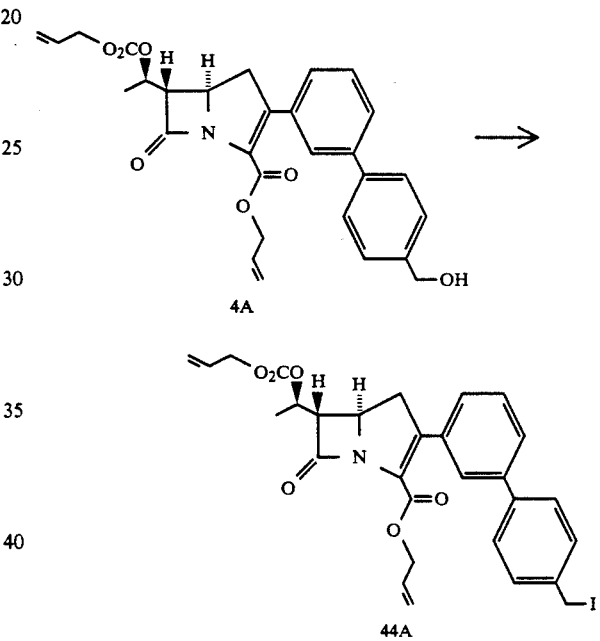

To a stirred solution of 47.3 mg (0.09 mmole) of alcohol 4A, prepared in Example 4, in 1 mL sieve dried CH$_2$Cl$_2$ at 0° C. under a nitrogen atmosphere was added sequentially 14.3 mg (0.14 mmole) of triethylamine and then 14 mg (0.12 mmole) of mesyl chloride. The mixture was stirred at 0° C. for 20 minutes and was then partitioned between EtOAc/ice/H$_2$O/2N HCl and the organic phase was separated, washed with saturated sodium chloride solution, dried over sodium sulfate, filtered, and evaporated to give 56.6 mg of crude mesylate intermediate.

The crude mesylate was dissolved in 1 mL acetone and stirred with 28.2 mg (0.19 mmole) of sodium iodide in the cold for a few minutes and then further, with the ice-H$_2$O bath removed, for 1.0 hour. After this time the mixture was partitioned between EtOAc/ice-H$_2$O/5% aqueous sodium thiosulfate solution, and the organic phase was separated, washed with brine, dried over anhydrous sodium sulfate, filtered, and evaporated to give 53.7 mg of crude product.

Purification by PLC, [1 development hexane-EtOAc (2:1)] gave 28.3 mg (49%) of oily iodide 44A; IR(CH$_2$Cl$_2$): 1785, 1750, 1725 cm$^{-1}$; NMR(CDCl$_3$) δ:

1.54 (d, J=6.4 Hz, CH₃), 3.26 (dd, 1-H-1), 3.36 (dd, 1-H-1), 3.46 (dd, 1-H-6), 4.32 (dt, 1-H-5), 4.55 (s, CH₂I), 7.3-7.62 (m, Ar-H); UV: $\lambda_{max}^{dioxane}$ 284 nm.

EXAMPLE 45

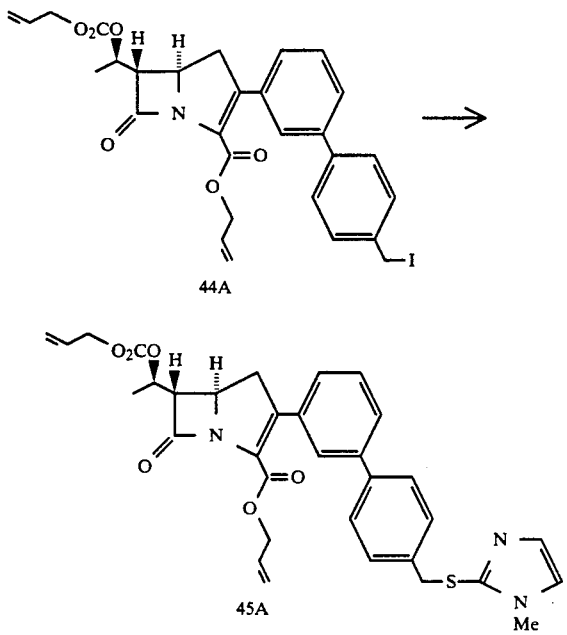

To a stirred solution of 40.6 mg (0.07 mmole) iodomethylbiphenylcarbapenem derivative from Example 44 in 1.5 mL acetonitrile at −20° C. under a nitrogen atmosphere was added 140 μL (0.07 mmole) of a freshly prepared stock solution of sodium 2-N-methylimidazolemercaptide in DMF which was prepared by the interaction of 250 mg (2.19 mmole) of N-methyl-2-mercaptoimidazole and sodium hydride in 5.5 mL of sieve dried DMF at 0° C. for 2 hours. The resulting mixture was stirred further at −20° C. for 15 minutes.

The mixture was partitioned between EtOAc/ice-H₂O and the organic phase separated, washed with brine, dried over Na₂SO₄, filtered, evaporated, and dried in vacuo to give 34.9 mg (88%) of product: IR (CH₂Cl₂) 1780, 1745, and 1720 cm⁻¹; 1.5 (d, CH₃), 3.3 (m, 2H-1), 3.32 (s, N—CH₃), 4.22 (s, —SCH₂), 4.31 (td, 1H-5), 4.68 (m, 2—OCH₂CH=CH₂), 5.26 (m, 1H-8 and 2—CH=CH₂), 5.88 (m, 2CH=CH₂), 6.88 (bs, 1-Im-H), and 7.1-7.6 (m, ArH and 1Im -H); UV: $\lambda_{max}^{dioxane}$ 278 nm, 315 nm (sh).

EXAMPLES 46-91

Employing the procedures described above, additional compounds of the present invention were prepared which are described in the table below.

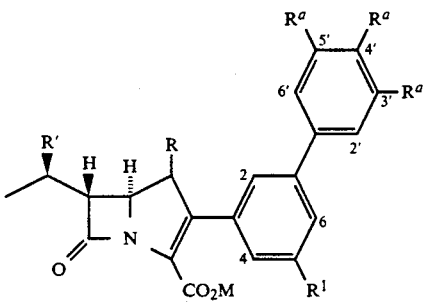

| | | | | $R^a$ | | | | |
|---|---|---|---|---|---|---|---|---|
| EX # | R' | R | 5 | 3' | 4' | 5' | M | $\lambda_{max}^{H_2O}$ (nm) |
| 46 | OH | H | H | H | H | H | K | 299, 252 |
| | OH | H | F | H | H | H | K | 300, 251 |
| | OH | H | OCH₃ | H | H | H | K | 302, 253 |
| | OH | H | OH | H | H | H | Na | 302, 251 |
| 50 | OH | H | SCH₃ | H | H | H | Na | 303, 254 |
| | OH | H | S(O)CH₃ | H | H | H | K | 302, 253 |
| | OH | H | SO₂CH₃ | H | H | H | Na | 306, 256 |
| | OH | H | CN | H | H | H | Na | 304, 254 |
| | OH | H | CO₂Na | H | H | H | Na | 300 |
| 55 | OH | H | CONH₂ | H | H | H | Na | 300, 255 |
| | OH | H | CO₂CH₃ | H | H | H | Na | 300 |
| | OH | H | OCOCH₃ | H | H | H | Na | 300, 253 |
| | OH | H | H | OH | H | H | Na | 290, 251 |
| | OH | H | H | F | H | H | Na | 300, 250 |
| 60 | OH | H | CH₂OH | H | H | H | Na | 300 |
| | OH | H | CHO | H | H | H | Na | 300 |
| | OH | H | SCH₂CH₂OH | H | H | H | Na | 302, 257 |
| | OH | H | SO₂CH₂CH₂OH | H | H | H | Na | 304, 254 |
| | OH | H | S(O)CH₂CH₂OH | H | H | H | Na | 304, 254 |
| 65 | OH | H | SO₂NH₂ | H | H | H | Na | 304, 254 |
| | OH | H | SO₂NHCH₃ | H | H | H | Na | 305 |
| | OH | H | SO₂N(CH₃)₂ | H | H | H | Na | 304, 254 |

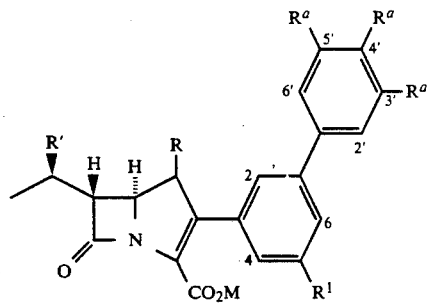

| EX # | R' | R | R$^a$ 5 | 3' | 4' | 5' | M | $\lambda_{max}^{H2O}$ (nm) |
|---|---|---|---|---|---|---|---|---|
|  | OH | H | SO$_2$N(∼OH)$_2$ | H | H | H | Na | 305 |
|  | OH | H | COCH$_3$ | H | H | H | Na | 300, 238 |
| 70 | OH | H | CONHCH$_3$ | H | H | H | Na | 300, 250 |
|  | OH | H | CON(CH$_3$)$_2$ | H | H | H | Na | 302, 252 |
|  | OH | H | Br | H | H | H | Na | 300, 255 |
|  | OH | H | SO$_2$CH=CH$_2$ | H | H | H | Na | 305, 256 |
|  | OH | H | H | OCONH$_2$ | H | H | Na | 297, 252 |
| 75 | OH | H | H | H | OH | H | Na | 300, 265 |
|  | OH | H | H | H | CH$_2$OH | H | K | 296, 257 |
|  | OH | H | F | H | CH$_2$OH | H | Na | 299 |
|  | OH | H | F | H | OCOCH$_3$ | H | Na | 300, 254 |
|  | OH | H | F | H | OH | H | Na | 300 sh, 265 |
| 80 | OH | H | F | H | OCONH$_2$ | H | Na | 300, 256 |
|  | OH | H | H | H | CN | H | Na | 274 |
|  | OH | H | H | H | CH=CHCONH$_2$ (trans) | H | K | 308 |
|  | OH | H | H | H | CH=CHCN (trans) | H | K | 309 |
|  | OH | H | H | H | SCH$_3$ | H | Na | 284 |
| 85 | OH | H | H | H | SOCH$_3$ | H | Na | 300, 268 |
|  | OH | H | H | H | SO$_2$CH$_3$ | H | Na | 300, 268 |
|  | F | H | H | H | CH$_2$OH | H | K | 298 |
|  | OH | H | H | H | CH$_2$SCH$_3$ | H | K | 302, 263 |
|  | OH | βMe | H | H | CH$_2$OH | H | K | 295 |
| 90 | OH | H | H | H | N-Me-imidazole-2-thiomethyl | H | Na | 269 |
| 91 | OH | βMe | H | H | H | H | K | 300 |

EXAMPLES 92–118

Following the procedures described above, further examples of compounds of the present invention may be prepared, as set out in the table below.

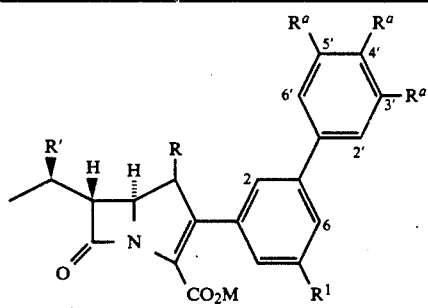

| EX # | R' | R | R$^a$ 5 | 3' | 4' | 5' | M |
|---|---|---|---|---|---|---|---|
| 92 | F | βMe | CN | H | SOCH$_3$ | H | Na |
|  | F | H | OH | H | SOCH$_3$ | H | Na |
|  | OH | βMe | F | H | SO$_2$NH$_2$ | H | Na |
| 95 | OH | H | H | H | OH | OH | Na |
|  | OH | H | F | H | OH | OH | Na |
|  | OH | H | CONH$_2$ | OH | OH | H | Na |
|  | OH | H | SO$_3$Na | H | H | H | Na |

-continued

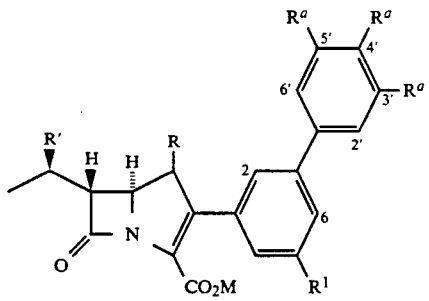

| EX # | R' | R | R$^a$ 5 | 3' | 4' | 5' | M |
|---|---|---|---|---|---|---|---|
|  | OH | H | PO$_3$Na | H | H | H | Na |
| 100 | OH | H | H | SO$_2$NH$_2$ | H | H | Na |
|  | OH | H | CF$_3$ | H | H | H | Na |
|  | OH | H | SCF$_3$ | H | H | H | Na |
|  | OH | H | SCN | H | H | H | Na |
|  | OH | H | SO$_2$CH$_2$CH$_2$CONH$_2$ | H | H | H | Na |
| 105 | HO | H | CONHCH$_2$CONH$_2$ | H | H | H | Na |
|  | HO | H | COCF$_3$ | H | H | H | Na |
|  | HO | H | COCH$_2$CONH$_2$ | H | H | H | Na |
|  | HO | H | OCH$_2$CH$_2$OH | H | H | H | Na |
|  | HO | H | H | H | OCH$_2$CH$_2$OH | H | Na |
| 110 | HO | H | H | H | SCH$_2$CH$_2$OH | H | Na |
|  | HO | H | H | H | SO$_2$CH$_2$CH2OH | H | Na |
|  | HO | H | H | H | S(O)CH$_2$CH$_2$OH | H | Na |
|  | HO | H | CH$_2$CONH$_2$ | H | H | H | Na |
|  | HO | H | SCH$_2$CONH$_2$ | H | H | H | Na |
|  | HO | H | PO$_2$NH$_2$ | H | H | H | Na |
|  | HO | H | SCH$_2$CH$_2$CN | H | H | H | Na |
| 118 | HO | H | SCH$_2$CH$_2$F | H | H | H | Na |

What is claimed is:

1. A compound of the formula:

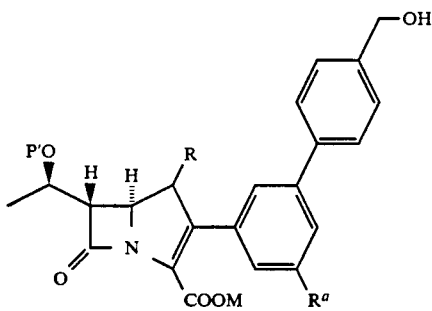

where
R is H or CH$_3$;
P' is a removable protecting group for hydroxy;
R$^a$ is selected from the group consisting of H, Cl, Br, I, SMe, CN, CHO, SOMe, SO$_2$Me, and OP'; and
M is a removable protecting group for carboxyl.

2. The compound of claim 1 wherein M is selected from the group consisting of benzhydryl, p-nitrobenzyl, 2-naphthylmethyl, allyl, benzyl, trichloroethyl, trimethylsilyl, t-butyldiphenylsilyl, phenacyl, p-methoxybenzyl, acetonyl, o-nitrobenzyl and 4-pyridylmethyl.

3. The compound of claim 1 wherein P' is selected from the group consisting of methoxy-t-butylphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

* * * * *